(12) United States Patent
Scheper et al.

(10) Patent No.: US 7,413,637 B2
(45) Date of Patent: Aug. 19, 2008

(54) SELF-CONTAINED, SELF-POWERED ELECTROLYTIC DEVICES FOR IMPROVED PERFORMANCE IN AUTOMATIC DISHWASHING

(75) Inventors: William Michael Scheper, Lawrenceburg, IN (US); Kenneth Nathan Price, Cincinnati, OH (US); Julia Elizabeth Ballas, Fairfield, OH (US); Mario Elmen Tremblay, West Chester, OH (US)

(73) Assignee: The Procter and Gamble Company, Cincinnati, OH (US)

( * ) Notice: Subject to any disclaimer, the term of this patent is extended or adjusted under 35 U.S.C. 154(b) by 657 days.

(21) Appl. No.: 10/222,575

(22) Filed: Aug. 16, 2002

(65) Prior Publication Data
US 2003/0213704 A1 Nov. 20, 2003

Related U.S. Application Data

(60) Provisional application No. 60/381,455, filed on May 17, 2002, provisional application No. 60/381,472, filed on May 17, 2002, provisional application No. 60/381,146, filed on May 17, 2002, provisional application No. 60/381,473, filed on May 17, 2002.

(51) Int. Cl.
*C25B 9/00* (2006.01)
*C25B 1/26* (2006.01)

(52) U.S. Cl. .............. 204/275.1; 204/276; 204/228.6; 204/229.2; 204/229.4; 204/229.6

(58) Field of Classification Search .............. 204/228.6, 204/229.2, 229.4, 229.6, 275.1, 276
See application file for complete search history.

(56) References Cited

U.S. PATENT DOCUMENTS

| 1,217,643 | A |   | 2/1917  | Schneider        |
|-----------|---|---|---------|------------------|
| 3,518,174 | A | * | 6/1970  | Inoue ........... 205/743 |
| 3,616,355 | A |   | 10/1971 | Themy et al.     |
| 4,048,047 | A |   | 9/1977  | Beck et al.      |
| 4,062,754 | A |   | 12/1977 | Eibl             |
| 4,100,052 | A |   | 7/1978  | Stillman         |
| 4,328,084 | A |   | 5/1982  | Shindell         |
| 4,402,197 | A |   | 9/1983  | Groult et al.    |
| 4,434,629 | A |   | 3/1984  | Bianchi et al.   |
| 4,481,086 | A |   | 11/1984 | Bianchi et al.   |

(Continued)

FOREIGN PATENT DOCUMENTS

EP      0 152 154 A2     8/1985

(Continued)

OTHER PUBLICATIONS

International Searching Authority, Patent Cooperation Treaty International Search Report, Nov. 26, 2003, 2 pages, International Application No. PCT/US 03/15483 by A. Lodato, ISA European Patent Office, PB 5818 Patentlaan 2, NL-2280 HV Rijswijk.

*Primary Examiner*—Arun S Phasge
(74) *Attorney, Agent, or Firm*—Julie A. McConihay; Ian S. Robinson; Kim William Zerby

(57) ABSTRACT

An automatic dishwashing appliance comprising an unattached electrolytic device which comprises an unattached electrochemical cell capable of generating electrolyzed water in the wash and/or rinse cycle, and more particularly to the unattached electrolytic device itself, methods of use, and articles of manufacture.

39 Claims, 11 Drawing Sheets

U.S. PATENT DOCUMENTS

| | | | |
|---|---|---|---|
| 4,493,760 A | 1/1985 | Bianchi | |
| 4,761,208 A | 8/1988 | Gram et al. | |
| 5,250,160 A | 10/1993 | Oksman et al. | |
| 5,314,589 A | 5/1994 | Hawley | |
| 5,395,492 A | 3/1995 | Schoeberl | |
| 5,439,576 A | 8/1995 | Schoeberl | |
| 5,534,120 A | 7/1996 | Ando et al. | |
| 5,753,098 A | 5/1998 | Bess, Jr. et al. | |
| 5,865,966 A | 2/1999 | Watanabe et al. | |
| 5,932,171 A | 8/1999 | Malchesky | |
| 5,947,135 A | 9/1999 | Sumida et al. | |
| 5,954,939 A | 9/1999 | Kanekuni et al. | |
| 6,921,743 B2 | 7/2005 | Scheper et al. | |
| 7,048,842 B2 | 5/2006 | Tremblay et al. | |
| 2002/0046957 A1 | 4/2002 | Hough et al. | |
| 2005/0067300 A1 | 3/2005 | Tremblay et al. | |
| 2006/0096618 A1 | 5/2006 | Price et al. | |
| 2006/0217280 A1 | 9/2006 | Scheper et al. | |

FOREIGN PATENT DOCUMENTS

| | | |
|---|---|---|
| EP | 0 761 156 A1 | 3/1997 |
| EP | 0 983 806 A1 | 3/2000 |
| GB | 2120282 * | 3/1983 |
| JP | 05-137689 | 6/1993 |
| JP | 07-039749 U2 | 7/1995 |
| JP | 1997122060 A | 5/1997 |
| JP | 1998033448 A | 2/1998 |
| JP | 1998057297 A | 3/1998 |
| JP | 1998178491 A | 6/1998 |
| JP | 1998179489 A | 7/1998 |
| JP | 10-272469 | 10/1998 |
| JP | 11-216172 | 8/1999 |
| JP | 2000-093965 | 4/2000 |
| JP | 2000116587 A | 4/2000 |
| JP | 2000-233184 | 8/2000 |
| JP | 2001-212060 | 8/2001 |
| JP | 2003-093311 | 4/2003 |
| JP | 2003-230525 | 8/2003 |
| WO | WO 00/34184 | 6/2000 |
| WO | WO 00/64325 | 11/2000 |

* cited by examiner

SELF-CONTAINED, SELF-POWERED ELECTROLYTIC DEVICES FOR IMPROVED PERFORMANCE IN AUTOMATIC DISHWASHING

This application claims benefit of the filing date of U.S. Provisional Application Nos. 60/381,455; 60/381,472; 60,381,146 and 60/381,473 all filed May 17, 2002. This application claims reference to U.S. Provisional Application No. 60/280,913, filed Apr. 2, 2001 and U.S. patent application Ser. No. 09/947,846, filed Sep. 6, 2001.

FIELD OF THE INVENTION

The present invention relates to an automatic dishwashing appliance comprising an unattached electrolytic device which comprises an unattached electrochemical cell capable of generating electrolyzed water in the wash and/or rinse cycle, and more particularly to the unattached electrolytic device itself, methods of use, and articles of manufacture. An automatic dishwashing appliance comprising an unattached electrochemical cell can be capable of producing electrolyzed water comprising an oxidizing agent for cleaning, sanitizing and stain removal of soiled tableware.

BACKGROUND OF THE INVENTION

Electrochemical cells for use in automatic dishwashing appliances are designed to operate by making use of the water electrolysis process wherein, at the anode-water interface, OH− being present in water due to electrolytic dissociation of water molecules donates an electron to the anode and can be thereby oxidized to oxygen gas which can be removed from the system. As a result, the H+ concentration can be enhanced at the anode-water interface so that H+ enriched acidic water can be produced. In a similar manner, at the cathode-water interface, H+ accepts an electron from the cathode and can be reduced to hydrogen to form hydrogen gas which can be similarly eliminated from the system so that the OH− concentration can be increased at the cathode-water interface whereby OH− enriched alkaline water can be generated. Further, when halogen ion containing water (such as, natural water containing sodium chloride or an aqueous solution of sodium chloride) is subjected to electrolysis, halogenated mixed oxidants are generated in the electrolyzed water.

The following references disclose use of electrochemical cells: U.S. Pat. Nos. 5,932,171; 4,481,086; 4,434,629; 4,493,760; 4,402,197; 5,250,160; 5,534,120; 5,865,966; 5,947,135; JP Application No. 10057297A; JP Application No. 10179489A; JP Application No. 10033448A; JP Patent No. 09122060; JP Patent No. 2000116587; JP Patent No. 10178491; and EP Application No. 0983806A1.

The following references are also related to electrolyzed water: U.S. Pat. Nos. 3,616,355; 4,048,047; 4,062,754; 4,100,052; 4,328,084; 4,761,208; 5,314,589; 5,395,492; 5,439,576; 5,954,939 (equiv. EP 711,730); and WO 00/34184.

U.S. Pat. No. 4,402,197 encompasses in-line generation of hypochlorite from saline using an attached, non-partitioned electrochemical cell. U.S. Pat. No. 5,534,120 describes an attached, non-partitioned electrochemical cell, which can optionally separate the acidic/alkaline ionized water streams separately in the treatment of dishware. U.S. Pat. No. 5,947,135 describes the use of an attached, partitioned electrochemical cell that produces separate anolyte/catholyte streams for cleaning and disinfection of tableware. JP Application No. 10033448A discloses the use of an attached electrochemical cell in conjunction with an alkaline cleaning agent containing enzymes to clean tableware.

A problem with using attached electrochemical cells in automatic dishwashers can be that the electrochemical cells eventually become fouled from scaling and no longer function efficiently which can be difficult to remedy. Several remedies have been proposed. For example, JP Application No. 10057297A and U.S. Pat. No. 5,954,939 reduce scale formation in the electrochemical cell by electrode polarity reversal. WO Patent Number 00/64325 and U.S. Pat. No. 4,434,629 incorporate the electrochemical cell as part of a water softening system to reduce scaling. U.S. Pat. No. 5,932,171 provides an electrode cleaning composition, such as a source of acid or other descaler, to purge the electrochemical cell. Such remedies to descaling of attached electrochemical cells in automatic dishwashing appliances in the above references can increase the manufacturing cost of the appliance (e.g. polarity reversal, water softeners) or are inconvenient, temporary fixes (e.g. cleaning solutions) that require regular consumer attention.

Another problem of attached electrochemical cells can be that consumers should buy brand new, often expensive, automatic dishwashing appliances to experience the benefits of using electrolyzed water. It has now surprisingly been found that the use of an unattached electrolytic device, comprising an electrochemical cell, offers an efficient and convenient alternative to the abovementioned problem. In this case, either the unattached electrolytic device itself or its replaceable components can be exchanged for new. For instance, a consumer can decide to replace the disposable electrochemical cell in the unattached electrolytic device. If the consumer later desires to replace the unattached electrolytic device itself, this can also be done. This can be especially advantageous in automatic dishwashing appliances where consumer convenience can be desired.

Furthermore, the unattached devices of the present invention can be used with existing residential and commercial automatic dishwashing appliances, allowing consumers to experience the benefits of electrolyzed water in their current appliance without having to upgrade.

SUMMARY OF THE INVENTION

In one aspect of the present invention, an automatic dishwashing appliance having a washing basin can comprise an unattached electrolytic device for treating tableware for improved cleaning, sanitizing and stain removal. The device can comprise (a) a body comprising at least one inlet port for collecting an aqueous electrolytic solution provided by the appliance; (b) an electrochemical cell, located within the body, comprising at least one inlet opening and one outlet opening, and at least one pair of electrodes defining a cell gap comprising a passage formed therebetween through which an aqueous electrolytic solution can flow; and (c) a source of electrical current supply for providing electrical current between the pair of electrodes; wherein said device is self-powered and self-contained; and wherein said cell is in fluid communication with said aqueous electrolytic solution of said washing basin via said inlet port of said body, said cell passage, and/or said outlet opening.

In another aspect of the present invention, an unattached electrolytic device for treating tableware can comprise replaceable and/or disposable feature(s) selected from the group consisting of replaceable component(s) of the unattached electrolytic device, products used with the device, and combinations thereof. Another aspect of the present invention relates to a non-buoyant, unattached electrolytic device for placement in the washing basin of an automatic dishwashing appliance for treating tableware with electrolyzed water to provide an improvement in cleaning, sanitizing, and/or stain removal.

In another aspect of the present invention, a method can comprise treating tableware or cleaning, sanitizing, and removing stains from tableware in an automatic dishwashing appliance. The method can comprise the steps of: (a) placing tableware in need of treatment into said appliance; (b) placing said unattached electrolytic device comprising a body comprising at least one inlet port for collecting an aqueous electrolytic solution provided by said appliance, an electrochemical cell comprising at least one inlet opening and one outlet opening, and at least one pair of electrodes defining a cell gap comprising a passage formed therebetween through which an aqueous electrolytic solution can flow, and a source of electrical current supply for providing electrical current between said pair of electrodes; (c) providing said aqueous electrolytic solution in fluid communication with said electrochemical cell via said inlet port of said body of said unattached electrolytic device; (d) operating said cell and/or device so that said electrochemical cell produces at least some electrolyzed water; (e) discharging said electrolyzed water into the washing basin of said appliance via said outlet opening of said cell; and (f) contacting said tableware in need of treatment with said electrolyzed water comprising wash and/or rinse liquor.

In yet another aspect of the present invention, an article of manufacture can comprise an item selected from the group consisting of replaceable component(s) of the unattached electrolytic device, products used with the device, and combinations thereof. The article of manufacture for an unattached electrolytic device can comprise a: (a) package; (b) replacement component for said unattached electrolytic device selected from the group consisting of a: (i) replacement electrochemical cell; (ii) replacement automatic dishwashing composition comprising a component selected from the group consisting of suds suppressor, perfume, bleach-scavenging agent, metal-protecting agent, and mixtures thereof; (iii) replacement product comprising a component selected from the group consisting of an electrolytic composition comprising chloride ions, an electrolytic composition comprising chlorite ions, electrolytic solution comprising salts having the formula $(M)_x(XO_2)_y$ and/or $(M)_x(X)_y$ wherein X can be Cl, Br, or I and wherein M can be a metal ion or cationic entity and wherein x and y are chosen such that the salt can be charge balanced, electrolysis precursor compound, an electrolysis precursor salt with low water solubility, an electrolysis precursor compound contained within a medium for controlled release, and mixtures thereof, wherein said product is optionally housed in a porous basket; (iv) replacement filter or screen for said unattached electrolytic device; (v) replacement elastomeric slit valve; and (vi) combinations thereof; and (c) information in association with said package comprising instructions to insert said replacement components in said electrolytic device.

The following description can be provided to enable any person skilled in the art to make and use the invention, and can be provided in the context of a particular application and its requirements. Various modifications to the embodiments will be readily apparent to those skilled in the art, and the generic principles defined herein can be applied to other embodiments and applications without departing from the spirit and scope of the invention. The present invention can be not intended to be limited to the embodiments shown. Thus, since the following specific embodiments of the present invention are intended only to exemplify, but in no way limit, the operation of the present invention, the present invention can be to be accorded the widest scope consistent with the principles, features and teachings disclosed herein.

It should be understood that every maximum numerical limitation given throughout this specification would include every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The various advantages of the present invention will become apparent to those skilled in the art after a study of the foregoing specification and following claims. The following specific embodiments of the present invention are intended to exemplify, but in no way limit, the operation of the present invention. All documents cited are, in relevant part, incorporated herein by reference; the citation of any document can be not to be construed as an admission that it can be prior art with respect to the present invention.

BRIEF DESCRIPTION OF THE DRAWINGS

The invention will now be explained in detail with reference to the accompanying drawings, in which.

DETAILED DESCRIPTION OF THE INVENTION

Definitions

Figure 1:
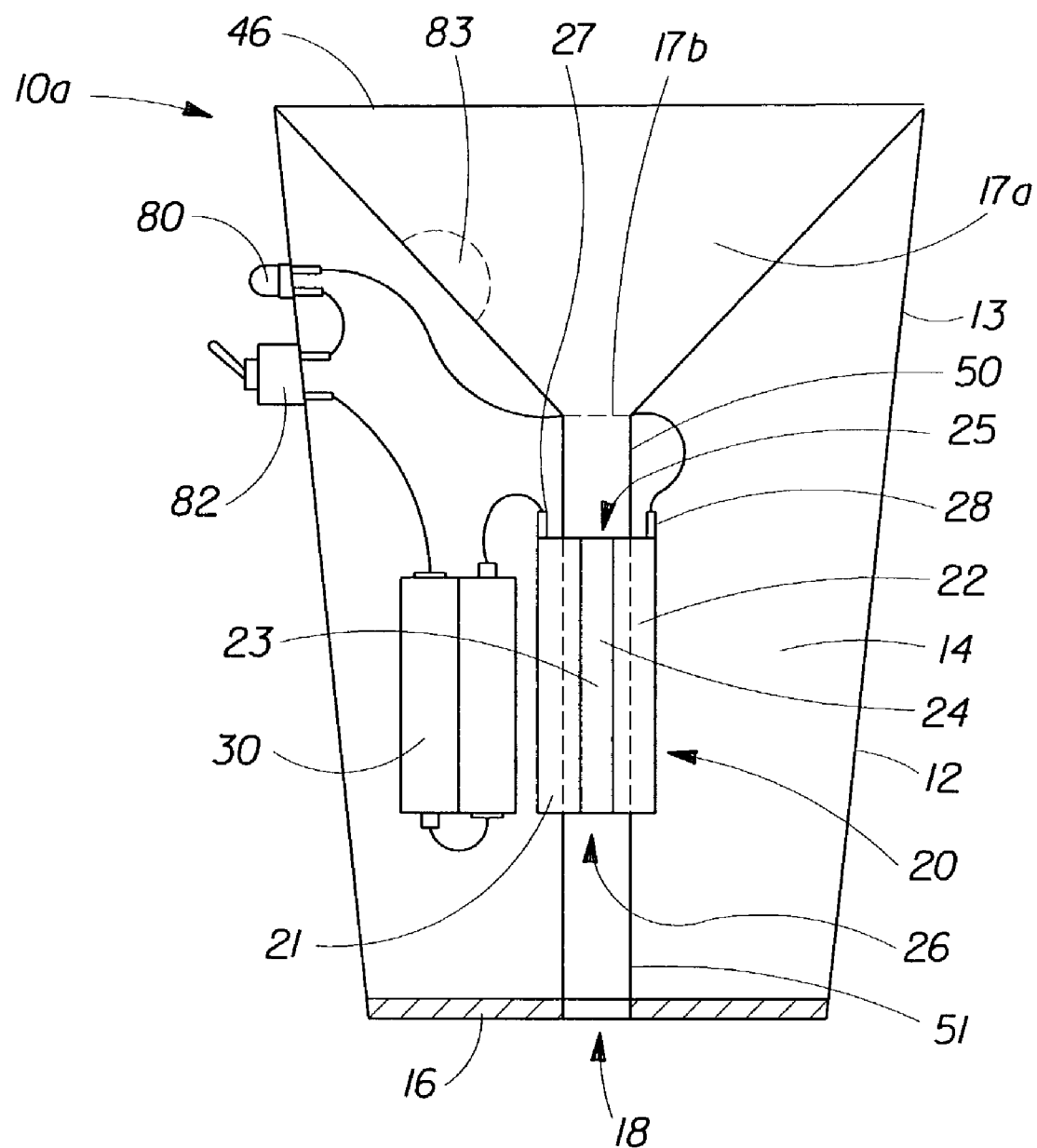
FIG. 1 shows an unattached electrolytic device.

"Attached" electrochemical cells and/or electrolytic devices are those cells and/or devices that are mechanically integrated into the automatic dishwashing appliance and which draw their electrical power from the electrical power supply of the appliance itself to produce electrolyzed water. Conversely, "unattached" electrochemical cells and/or electrolytic devices are those cells and/or devices that are self-powered and self-contained and which draw their electrical power from the unattached electrolytic device itself and/or alternatively from a building's electrical power supply to produce electrolyzed water in an automatic dishwashing appliance. An unattached electrolytic device can be removably placed in any automatic dishwashing device and/or countertop sink reservoir for treating tableware without having to install the device permanently. It can be easily removed from the appliance or countertop sink reservoir and can be placed in alternative sites for treatment of tableware as needed.

"Self-powered" means that a device itself can comprise the source of electrical or other power necessary for the defined functions of the device, which source can include, but can be not limited to, the electrical current supply for the electrochemical cell, the power for any pumping means, the power for any propulsion means, the power for any indication or control means, and the like. However, the self-powered device can alternatively obtain power from the building's electrical current supply via a rectifier that converts AC to DC that can plug into the electrical outlet.

"Self-contained" means that the device comprises elements substantially contained as a single article or unit, and do not necessarily require physical connection outside the reservoir with external power or propulsion means through wires, tethers, etc. However, the self-contained device can alternatively obtain power from the building's electrical current supply.

"Reservoir" means any body of water artificially confined. Examples include the wash and/or rinse liquor located in the washing basin of an automatic dishwashing appliance or wash and/or rinse water in a counter-top sink.

"Non-buoyant" means negatively buoyant (i.e., the body and/or device will not float to the surface of the reservoir electrolytic solution but will sink to the bottom of the reservoir electrolytic solution) and neutrally buoyant (i.e., the body and/or device will remain submerged and substantially stationary in the reservoir electrolytic solution). A "buoyant" body and/or device will float quickly to the surface of the reservoir electrolytic solution. The electrolytic devices described herein can be buoyant, non-buoyant, or neutrally buoyant.

"Robust" means that the cell and/or device can be designed for longer operating life, being less prone to fouling and scaling than conventional cells and/or devices.

"Fluid communication" means that electrolytic solution can flow between at least two objects defined herein.

"Sterilization" means the destruction of all microbial life, including bacterial spores.

"Sanitization" or "disinfection" means the elimination of nearly all microbial forms, but not necessarily all. Sanitization and/or disinfection do not ensure overkill and lacks the margin of safety achieved by sterilization.

"Treatment" means contacting tableware in need of treatment with tap water, wash and/or rinse liquor, recirculated wash and/or rinse liquor, or mixtures thereof comprising at least some electrolyzed water for purposes of providing the benefits of tableware cleaning, sanitization and stain removal. The treatment of tableware can be via an automatic dishwashing appliance or by hand, including but not limited to, hand dishwashing, dish pretreatment, dish post-treatment, and combinations thereof.

"Tableware" means any type of dishware and/or cookware, including, but not limited to, those made from glass, ceramic, metal, wood, porcelain, etc., as well as, any type of silverware which includes all types made from metal, wood, glass, ceramic, porcelain, etc. Tableware can include, but can be not limited to, cooking and eating utensils, dishes, cups, bowls, glasses, silverware, pots, pans, etc.

"Electrolytic solution" means an aqueous composition capable of being electrolyzed by the electrochemical cell and/or electrolytic device described herein. In its broadest use in the present invention, an aqueous electrolytic solution can be any chemically compatible solution that can flow through the passage of the electrochemical cell, and that contains sufficient electrolytes to allow a measurable flow of electricity through the solution. Water, except for deionized water, can be a preferred electrolytic solution, and can include: sea water; water from rivers, streams, ponds, lakes, wells, springs, cisterns, etc., mineral water; city or tap water; rain water; and brine solutions. An aqueous electrolytic solution of the present invention can be chemically compatible if it does not chemically explode, burn, and/or rapidly evaporate when placed inside the cell and/or device, or if it does not rapidly corrode, dissolve, or otherwise render the cell and/or device unsafe or inoperative, in its intended use.

"Recirculation" means to circulate again, such as the wash and/or rinse liquor in the washing basin of an automatic dishwashing appliance.

Unattached Electrolytic Device

Figure 2:
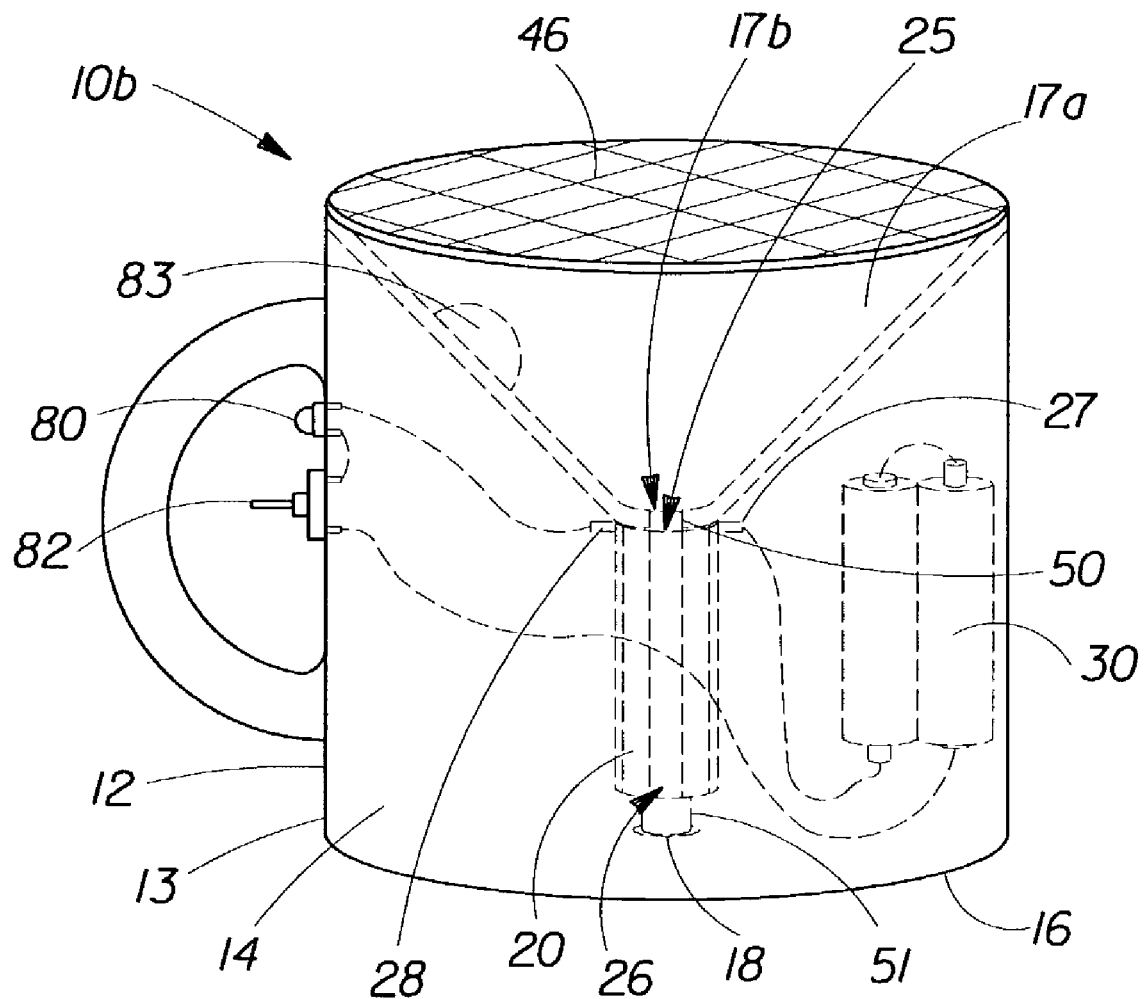
FIG. 2 shows an unattached electrolytic device.

FIG. 1 and FIG. 2 both show non-limiting examples of unattached electrolytic devices, 10a and 10b, respectively, having a body, 12, that can have a substantially continuous outer surface, 13, except for the inlet port, 17a, which can be covered by a detachable filter or screen, 46, to minimize fouling of the electrochemical cell, 20, due to the large debris load during the collection of electrolytic solution in the wash and/or rinse cycle of the automatic dishwashing appliance. The unattached electrolytic device, 10a or 10b, can also comprise a product or local source of halogen ions, 83, in the form of a slowly dissolving solid pellet. The base, 16, of the unattached electrolytic device, 10a or 10b, provides stability to the body and ensures that the device, 10a or 10b, remains positioned substantially vertical in the automatic dishwashing appliance so that the aqueous electrolytic solution can be collected by the unattached electrolytic device, 10a or 10b. The unattached electrolytic device, 10a or 10b, can comprise an inlet port, 17a, connected to a funnel-shaped portion, 17b, which can be connected to a tube or duct, 50, which can be connected to an electrochemical cell, 20, having an inlet opening, 25, and an outlet opening, 26. The outlet opening, 26, can be connected to a tube or duct, 51, which can be connected to the outlet port, 18, located on the base, 16.

The unattached electrolytic device, 10a or 10b, can also comprise a source of electrical current supply, 30, which can be connected to an on-off switch, 82, optionally comprising a timer/sensor (not shown), and to an indicator lamp, 80, that indicates to the consumer that either the device, 10a, and/or the batteries, 30, are operational and/or that the batteries are low. The electrochemical cell, 20, can comprise at least one pair of electrodes (an anode, 21, and a cathode, 22), defining a cell gap, 23, wherein a cell passage, 24, can be formed therebetween through which wash and/or rinse liquors comprising water from the appliance can flow. The electrochemical cell, 20, can be in fluid communication with the aqueous electrolytic solution, comprising the wash and/or rinse liquors from the appliance, via the inlet port, 17a, of the body, 12.

The unattached electrolytic device, 10a or 10b, has a source of electrical current supply (batteries), 30, which provides the current used by the electrochemical cell, 20, to the anode lead, 27, and the cathode lead, 28, of the electrochemical cell, 20, to generate electrolyzed water in the cell passage, 24. The water collected by the inlet port, 17a, flows by gravity through the electrochemical cell, 20, and out the outlet port, 18, via a tube or duct, 51, which connects the outlet opening, 26, thus allowing release or discharge of at least some electrolyzed water as a discharge effluent via the outlet opening, 26, of the electrochemical cell, 20, itself and/or the outlet port, 18, of the unattached electrolytic device, 10a or 10b, into the appliance during operation.

When the electrochemical cell, 20, can be positioned inside the body, 16, the inlet opening 25 can be placed into fluid communication with the aqueous electrolytic solution comprising wash and/or rinse liquor via at least one inlet port 17a in the outer surface of the body, 12, which can be connected to a funnel-shaped portion, 17b. The funnel-shaped portion, 17b, can be connected to a tube or duct, 50, that connects to the funnel-shaped portion, 17b, with the inlet opening, 25, of the electrochemical cell, 20. Likewise, the body, 12, can have an outlet port, 18, that can be in fluid communication between the outlet opening, 26, and with the wash and/or rinse liquor of the automatic dishwashing appliance via a tube or duct, 51.

Figure 3:
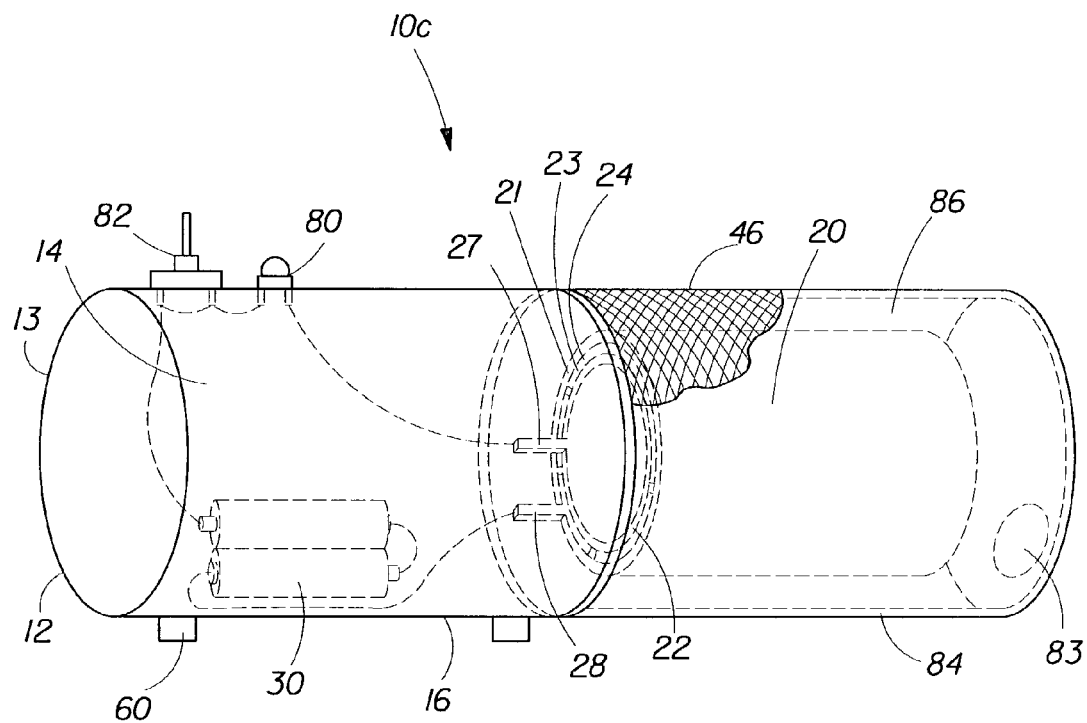
FIG. 3 shows an unattached electrolytic device.
Figure 4:
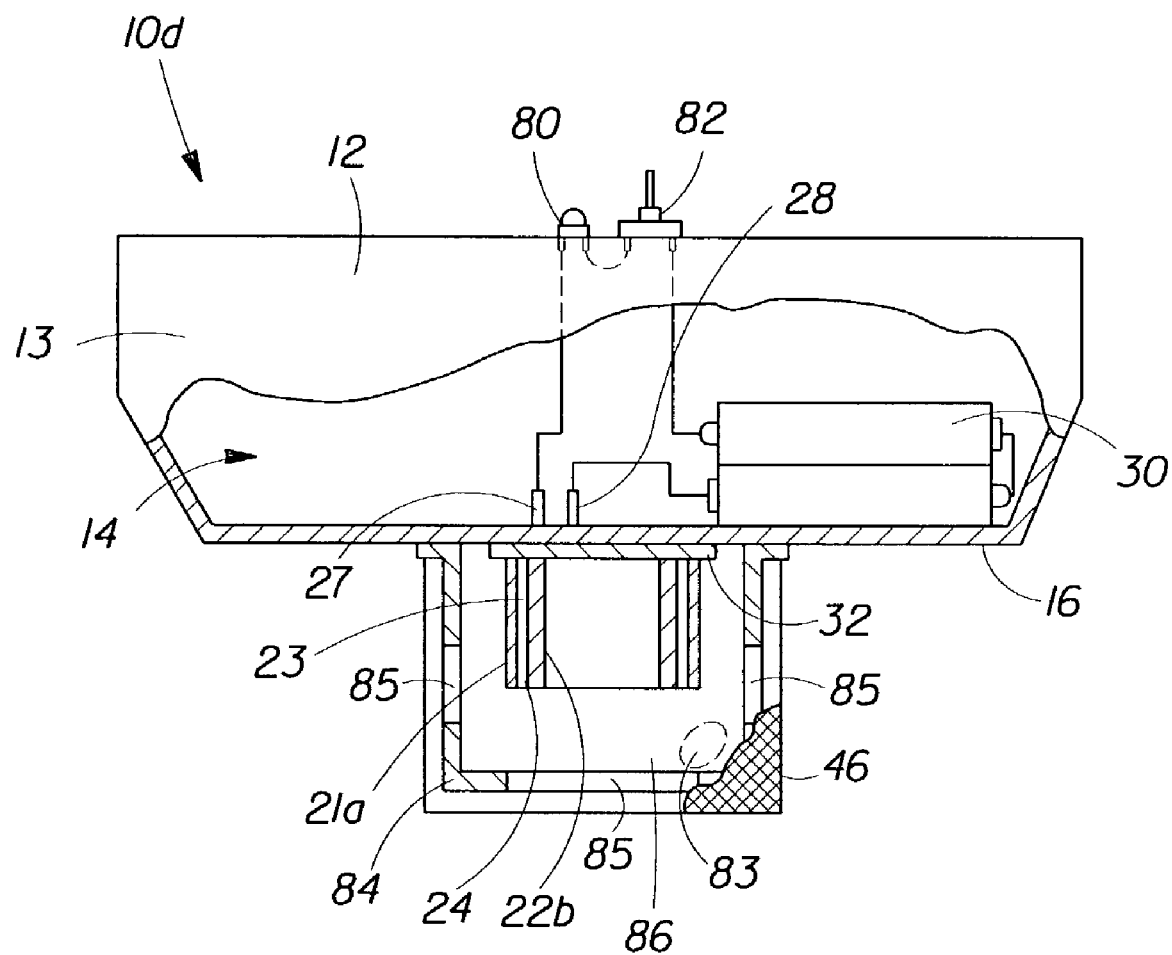
FIG. 4 shows an unattached electrolytic device.

Another embodiment of the present invention relates to a non-buoyant, unattached electrolytic device, 10c, 10d or 10e, comprising a form that can be suitable for immersion into a reservoir, like the washing basing of an automatic dishwashing appliance or countertop sink for purposes of treating wash and/or rinse liquor for applications selected from the group consisting of automatic dishwashing, hand dishwashing, dish pretreatment, dish post-treatment, and combinations thereof FIG. 3 and FIG. 4 show another embodiment of the present invention comprising an open-chamber electrolytic device, 10c, and 10d, respectively, which use an electrochemical cell, 20, that has an open chamber, 86. The unattached, open-chamber electrolytic device, 10c and 10d respectively, comprise an electrochemical cell, 20, particularly useful in the practice of the invention in reservoirs of electrolytic solution, including the washing basin of the automatic dishwashing appliance, sinks, buckets, and other containers of water for treating tableware. The open chamber, 86, can be covered by a detachable filter or screen, 46, to minimize fouling of the electrochemical cell, 20, due to the large debris load during the collection of electrolytic solution in the wash and/or rinse cycle of the automatic dishwashing appliance. The detachable filter or screen, 46, can be removably attached to the filter housing, 84, which can comprise multiple openings, 85 as in FIG. 4, to allow for free flow of the aqueous electrolytic solution to the electrodes, or comprise at least one opening in FIG. 3. Examples of open-chamber electrochemical cells include those described in U.S. Pat. No. 4,337,136 (Dahlgren), U.S. Pat. No. 5,013,417 (Judd), U.S. Pat. No. 5,059,296 (Sherman), and U.S. Pat. No. 5,085,753 (Sherman). The unattached electrolytic device, 10c or 10d, can also comprise a product or local source of halogen ions, 83, in the form of a slowly dissolving solid pellet.

The aqueous electrolytic solution can flow into the electrochemical cell, 20, via the open chamber, 86, to the anode, 21, from various directions. The halogenated salt in the aqueous electrolytic solution can be contained in the reservoir solution, or can be delivered into the reservoir solution locally as a local source of halogenated salt, 83, or from a porous basket comprising at least one product, 115, (see FIG. 6) as described below. The product can be selected from a solid electrolysis precursor compound, electrolysis precursor compound matrix of low water solubility, electrolysis precursor compound with a controlled release matrix, and mixtures thereof.

Figure 5:
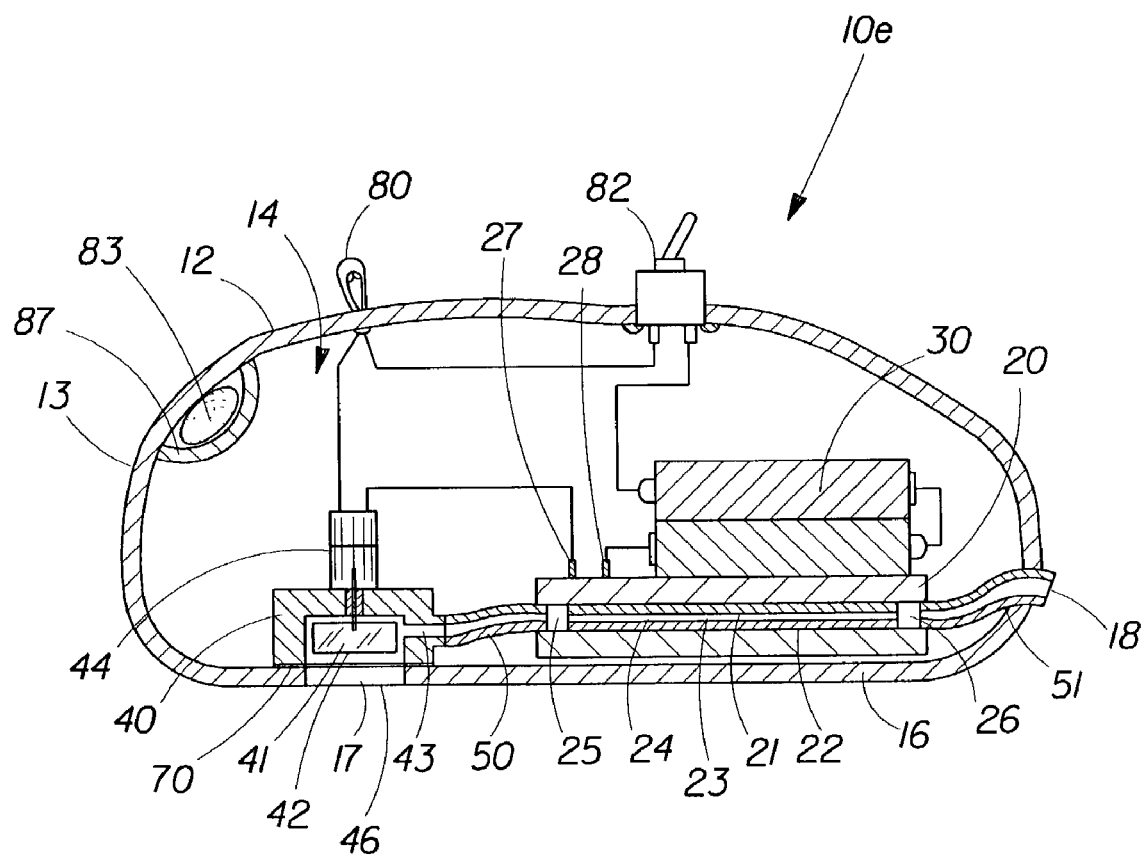
FIG. 5 shows an unattached electrolytic device.

FIG. 5 can be an unattached electrolytic device, 10e, having a body, 12, with a substantially continuous outer surface, 13, except for the inlet port, 17, which can be covered by a removably attached filter or screen, 46, to minimize fouling of the electrochemical cell, 20, due to the potential for a large debris load to be present during the collection of electrolytic solution in the wash and/or rinse cycle of the automatic dishwashing appliance. The body, 12, into, or onto, which the other elements are positioned, can be any open or closed object that can contain one or more of the other elements of the unattached electrolytic device, 10e, including an electrochemical cell, 20, an electrical current supply, 30, an impeller pump, 40, comprising a pump motor, 44, pump chamber, 41, pump inlet, 42, pump outlet, 43. The body, 12, can be made of any material that can be compatible with the aqueous electrolytic solution, and the device's use. The body, 12, can be preferably made of plastics, including PVC, polyethylene, polypropylene, other polyolefins, foam plastics, rubberized plastics, and styrofoam; metals including stainless steel, and others; and can even use wood or paper board including coated paperboard, depending upon the use. Preferred are durable, resilient plastics that can help to protect the internal components from external impact and forces that might otherwise damage them.

The unattached electrolytic device, 10e, can also comprise a source of electrical current supply, 30, which can be connected to an on-off switch, 82, optionally comprising a timer/sensor (not shown), and to an indicator lamp, 80, that indicates to the consumer that either the device, 10e, and/or the batteries, 30, are operational and/or that the batteries are low. The electrochemical cell, 20, can comprise at least one pair of electrodes (an anode, 21, and a cathode, 22), defining a cell gap, 23, wherein a cell passage, 24, can be formed therebetween through which wash and/or rinse liquors comprising water from the appliance can flow. The electrochemical cell, 20, can be in fluid communication with the aqueous electrolytic solution, comprising the wash and/or rinse liquors from the appliance, via the inlet port, 17a, of the body, 12.

The unattached electrolytic device, 10e, has a source of electrical current supply (batteries), 30, which provides the current used by the electrochemical cell, 20, to the anode lead, 27, and the cathode lead, 28, of the electrochemical cell, 20, to generate electrolyzed water in the cell passage, 24. The water collected by the inlet port, 17, can be pumped through the electrochemical cell, 20, via the impeller pump, 40, and out the outlet port, 18, via a tube or duct, 51, which connects the outlet opening, 26, thus allowing release or discharge of at least some electrolyzed water as a discharge effluent via the outlet opening, 26, of the electrochemical cell, 20, itself and/or the outlet port, 18, of the unattached electrolytic device, 10e, into the appliance (not shown) during operation.

The body, 12, can be made in almost any shape, including spheres and ovals, cubes, and rectilinear shapes. A preferred shape can be that of a cylinder, ellipse, such as, a saucer shape, or any other shape, especially those for use in an automatic dishwashing appliance washing basin. The body, 12, can take any shape or form that can be conducive to efficient electrolysis during the operation of the automatic dishwashing appliance. As there are many different shapes and forms that can work, the body, 12, of the shape and form of the device can be limited only by its ability to be placed within an operating automatic dishwashing appliance without interfering with the function or performance of the appliance itself. The outer body, 12 should be constructed of material that can be resistant to the corrosive environment of the automatic dishwashing appliance. It can be made of a hard plastic, stainless steel, and mixtures thereof.

Preferred devices comprise a housing that can be sealed or can be sealable to prevent electrolytic solution from entering the housing, except as intended (such as through the inlet port 17a). The body, 12 can be preferably a closed body having a confined space within the body, 14, to contain one or more of the other components of the unattached electrolytic device, 10e, and can be most preferable water-proof to prevent the solution (e.g., water) from entering into the body, 12 (except through the inlet port 17), thereby preventing short circuiting or other damage to an electrical current supply, 30, and any pumping means, propulsion means, etc. The body can have an inlet port, 17, through its outer surface through which electrolytic solution can pass through to the electrochemical cell, 20, contained therein.

In addition, the body, 12, can also comprise at least one sealed or sealable compartment, 14. The at least one sealed or sealable compartment, 14, can be openable so as to allow removal and/or replacement of the electrochemical cell, 20, the electrical current supply (battery), 30, the pump, 40, and combinations thereof. The at least one sealed or sealable compartment, 14, can be separate and independent from other compartments or other sealed or sealable compartments. The unattached electrolytic device, 10a or 10b, can also comprise a product or local source of halogen ions, 83, in the form of a slowly dissolving solid pellet. An additional sealed or sealable compartment, 86, can exist to allow for storage of at least one product, 83, for release, or any other purpose.

The at least one sealed or sealable compartment, 14, can have one or more removable covers for openings (not shown), through which components, can be removed, installed, or replaced, and which can be made liquid sealable. The sealed or sealable compartment, 14, within the body, 12, serves to prevent liquid, such as the aqueous electrolytic solution, from entering.

The internal volume of the body, 12, should be sized to provide both an sealed or sealable compartment, 14, for the components, and yet ensure the device, 10e, can be properly buoyant taking into account the combined weight of the body, 12, and its components. For negatively buoyant devices, a target maximum submersion of the device can be about 100%. For positively buoyant devices, a target maximum submersion of the device can be about 80%, which means the volume of the device that can be below the surface of the water should be 80% or less. For positively buoyant devices, the weight of the device should be 80% or less of the weight in water that the volume of the device will occupy. Small devices that are more convenient to handle can advantageously use miniaturized pumps, electrochemical cells, and battery sets that deliver high productivity and efficiency.

In addition, the body, 12, can also comprise a means for allowing recharging of rechargeable internal batteries via such means as a plug or port (not shown) such that the consumer can conveniently recharge the batteries without opening said compartment or compartments.

Another embodiment of the present invention can comprise a spray nozzle (not shown) having in the spray solution pathway leading to the spray nozzle, an electrochemical cell, with an anode having a surface area of from about 0.1 cm$^2$ to about 20 cm$^2$, more preferably from about 2 cm$^2$ to about 8 cm$^2$. A trigger-actuated pump or an electrically-driven motorized pump can pump the spray solution to the electrochemical cell. Such spray pump units will typically spray from about 100 to about 300 cc/min. of spray solution.

The spray solution will generally comprise a halogenated salt solution and at least one surfactant selected from the group consisting of: anionic, nonionic, cationic, zwitterionic, amphoteric or soap surfactants. The spray solution can optionally comprise one or more other ingredients selected from enzymes, auxiliary bleach ingredients, electrolytes, builders and sequestering agents, chelants, brighteners, colorants, pH buffering agents, perfumes, odor absorbing ingredients, and mixtures thereof.

Figure 6:
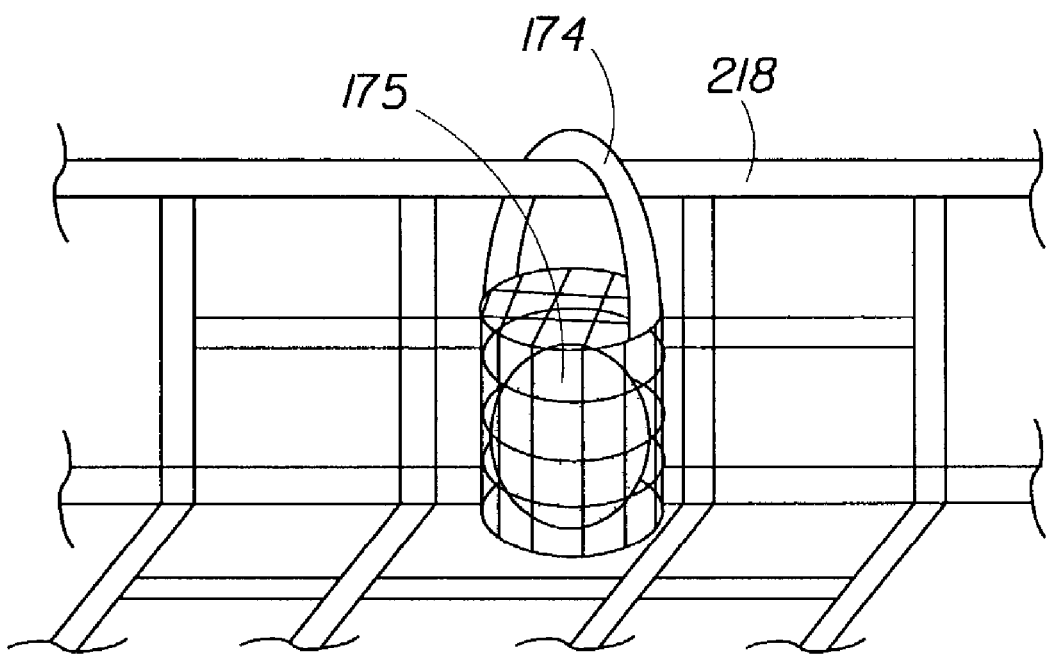
FIG. 6 shows an example of a product container.

FIG. 6 shows an example of a product, 175, stored via an porous basket, 174, such as a coated plastic wire a porous basket, which can be removably attached to the rack, 115, of the automatic dishwashing appliance, or by any other means, so as to allow delivery of the halogenated salt to the aqueous electrolytic solution during operation of the appliance, as further herein described.

Automatic Dishwashing Appliance Comprising an Unattached Electrolytic Device.

Figure 7:
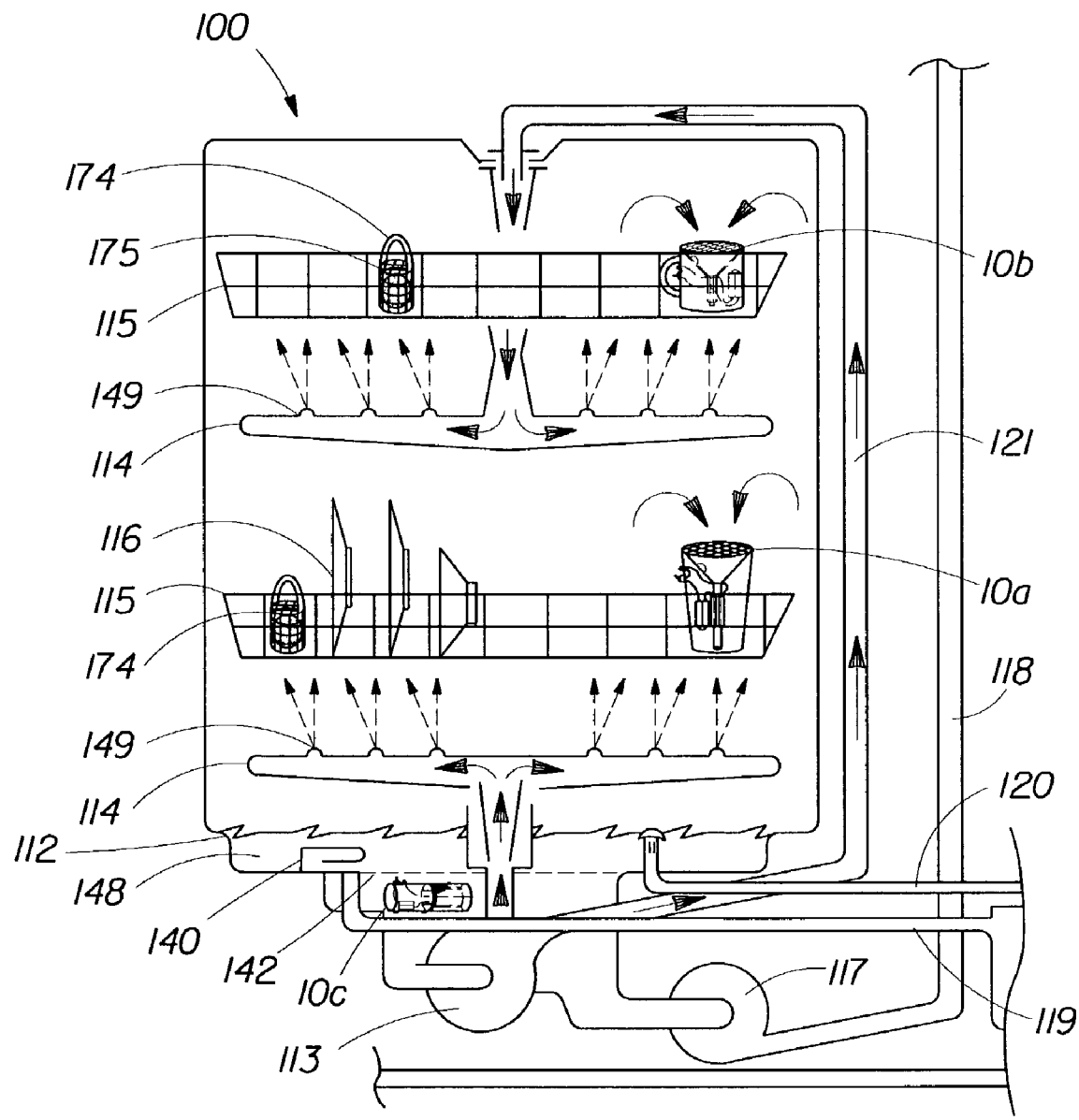
FIG. 7 shows an automatic dishwashing appliance comprising an immersed, unattached electrolytic device and a product container.

FIG. 7 shows a conventional automatic dishwashing appliance, 100, comprising a variety of unattached electrolytic devices, 10a, 10b and 10c, for illustration purposes only. The unattached electrolytic device of either FIG. 1 and/or FIG. 2 can be placed in the rack, 115, while the negatively buoyant, unattached electrolytic device of either FIG. 3, FIG. 4 and/or FIG. 5 can be placed in the washing basin of automatic dishwashing appliance to ensure the benefit of electrolyzed water in an existing automatic dishwashing appliance, 100.

A cross sectional view of part of a conventional dishwasher 100, shown in FIG. 7, includes a front door (not shown) which can be opened and closed and through which tableware to be washed can be taken in and out, a rack, 115, for accommodating tableware, 116, to be washed, a washing basin, 112, located under rack, 115, for storing washing water, 148, a rotary washing nozzle, 114, protruding at approximately the center of washing basin, 112, a filter, 142, for collecting the food debris and the like separated from tableware, 116, by washing, a plurality of injection openings, 149, provided on washing nozzle, 114, a heater, 140, provided within washing basin, 112, for heating washing water, 148, a washing pump, 113, for supplying washing water, 148, to washing nozzle, 114, a drain pump, 117, for discharging washing water, 148, to a drain pipe, 118, a water feed pipe, 119, for feeding washing water, 148, a water feed valve (not shown) for controlling the feeding of water from water feed pipe, 119, a drying fan (not shown) for blowing air for drying of washed tableware, 116, an air heater, (not shown) for heating air blowing from drying fan (not shown), a heat exchange duct (not shown) for discharging the supplied heated air from a main body to the outside thereof and returning water obtained by condensing vapor to washing basin, 112, and a controller (not shown) having a CPU for controlling the entire dishwasher, 100. The washing operation of dishwasher, 100, will now be described briefly. First, front door (not shown) can be opened, an unattached electrolytic device, 10a or 10b, can be placed at a proscribed position of rack, 115, (the non-buoyant, unattached electrolytic device, 10c, 10d, or 10e, can be placed in a proscribed position in the washing basin, 112, away from the heater, 140). A porous basket, 174, containing a product, 175, such as a pro-oxidant salt, can be placed at a proscribed position of rack, 115. Tableware, 116, to be washed can be placed at a proscribed position of rack, 115. Rack, 115, can be placed above washing basin, 112, and thereafter, a specific automatic dishwashing detergent can be placed in and operation can be started. Then, a proscribed amount of washing water, 148, can be supplied through water feed pipe, 119, into washing basin, 112, by "open" operation of water feed valve (not shown).

Thereafter, washing water, 148, pressurized by operation of washing pump, 113, can be injected together with at least some of the dissolved product, 175, and detergent from injection openings, 149, of rotary washing nozzle, 114, to the unattached electrolytic device, 10a or 10b, which collects and electrolyzes the washing water, 148, that passes through the unattached electrolytic device, 10a or 10b, discharging the electrolyzed washing water, 148, back to the washing basin for subsequent injection. The injected electrolyzed washing water, 148, contacts the tableware, 116, via the injection openings, 149, whereby washing can be carried out. Thereafter, a proscribed amount of rinsing water, 148, can be supplied through water feed pipe, 119, into washing basin, 112, by "open" operation of water feed valve (not shown). Thereafter, rinsing water, 148, pressurized by operation of washing pump, 113, can be injected together with at least some of the dissolved product, 175, and detergent from injection openings, 149, of rotary washing nozzle, 114, to the unattached electrolytic device, 10a or 10b, which collects and electrolyzes the rinsing water, 148, that passes through the unattached electrolytic device, 10a or 10b, discharging the electrolyzed rinsing water, 148, back to the washing basin for subsequent injection. The electrolyzed rinsing water, 148, contacts the tableware, 116, via the injection openings, 149, whereby rinsing can be carried out. The rinsing step(s) can be followed by drying step(s).

In dishwasher, 100, when the washing step can be started, washing water, 148, can be contaminated with dirt attached to tableware, 116, and the food debris can be filtered by filter, 142. In dishwasher, 100, when the rinsing step can be started, rinsing water, 148, can be heated with a heater, 140, provided within washing basin, 112, for heating rinsing water, 148, before being injected to tableware, 116, by washing pump, 113.

One embodiment of the present invention relates to an automatic dishwashing appliance comprising an unattached electrolytic device for treating tableware to provide an improvement in cleaning, sanitizing, and/or stain removal, wherein said device can comprise (a) a body comprising at least one inlet port for collecting an aqueous electrolytic solution provided by said appliance; (b) an electrochemical cell, located within said body, comprising at least one inlet opening and one outlet opening, and at least one pair of electrodes defining a cell gap comprising a cell passage formed therebetween through which said aqueous electrolytic solution can flow; and (c) a source of electrical current supply for providing electrical current between said pair of electrodes; wherein said device can be self-powered and self-contained; wherein said electrochemical cell can be in fluid communication with said aqueous electrolytic solution via said inlet port of said body.

In one embodiment of the present invention, the cell and/or device, 10a, 10b, 10c, are in fluid communication with the aqueous electrolytic solution in the washing basin, 112, which can comprise tap water, wash and/or rinse liquors, and mixtures thereof, thus allowing release, discharge, or propulsion of at least some electrolyzed water as an effluent outside the unattached, self-powered, self-contained electrolytic device, 10a, 10b, 10c, into the washing basin, 112, of the appliance, 100.

It can be contemplated by the inventors that any of the features and/or embodiments of the unattached electrolytic device (10a, 10b, 10c, 10d, 10e of FIGS. 1-5) described herein can also be used in conjunction with any conventional automatic dishwashing appliance of the present invention.

Energy-Saving Automatic Dishwashing Appliance Having an Unattached Energy-Saving Cell and/or Device Another embodiment of the present invention relates to an energy-saving appliance comprising an unattached, integrated, energy-saving cell and/or device; wherein the energy-saving cell can comprise at least one inlet opening and one outlet opening, and at least one pair of electrodes defining at least one cell gap comprising at least one cell passage formed therebetween through which an aqueous electrolytic solution can flow. The energy-saving appliance has a total energy consumption of less than about 1.8 kWh per complete operating cycle and/or less than about 600 kWh per year, preferably less than about 1.7 kWh per operating cycle and/or about 555 kWh per year, most preferably less than about 1.2 kWh per operating cycle and/or about 400 kWh per year. The total energy consumption of the appliance includes any energy used to heat wash and/or rinse liquor in the appliance.

Another embodiment of the present invention relates to an energy-saving appliance further comprising an incoming tap water supply comprising at least a cold water supply. The incoming tap water supply can also consist essentially of a cold water supply. A water-heating booster, a water-heating element, and/or other means of providing additional thermal energy to the incoming tap water supply are optional, and not required for the sanitization of tableware. The energy-saving cell of the present invention can be selected from the group consisting of partitioned, non-partitioned, robust, recirculating, non-recirculating, and combinations thereof.

Another embodiment of the present invention relates to an energy-saving appliance further comprising a storage means for storing at least one product prior to its release. The storage means comprising at least one sealed or sealable compartment for housing and delivering the product to the wash and/or rinse liquor of the appliance, such that the product can be discharged in conjunction with at least one predetermined point in time during the wash and/or rinse cycle of the appliance, wherein when the sealed or sealable compartment houses the product the sealed or sealable compartment can be optionally recloseable such that the contents of the sealed or sealable compartment are not contaminated by an external medium.

Another embodiment of the present invention relates to an energy-saving appliance further comprising a means for communicating to the consumer when it can be time to refill and/or replace a component selected from the group consisting of an energy-saving cell, energy-saving device comprising the energy-saving cell, product refill and/or replacement cartridge, filter, elastomeric slit valve, porous basket comprising a product for dispensing, and combinations thereof.

Figure 8:
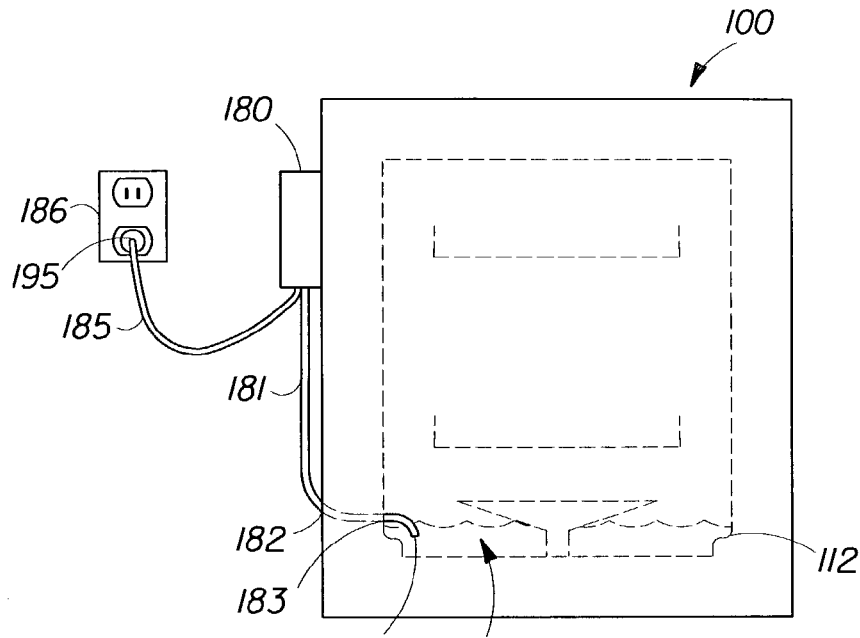
FIG. 8 shows an automatic dishwashing appliance comprising a non-immersed, unattached electrolytic device powered by an external power source.

Another embodiment of the present invention relates to an automatic dishwashing appliance comprising a non-immersed, unattached electrolytic device as shown in FIG. 8. In this embodiment the electrolytic device, 180, comprising an electrochemical cell (not shown) and optionally a pump (not shown) is physically located outside the wash basin, 112, of the automatic dishwashing appliance, 100, but is in fluid communication with the rinsing or washing water, 148, via a multi-compartmented tube, 181, (or alternatively, via two single-channeled tubes) which connects to the electrolytic device, 180, on one end, and on the other end is immersed in the washing water, 148, of the wash basin, 112. The multi-channeled tube, 181, enters the exterior body of the automatic dishwashing appliance, 100, via an optional, externally sealed penetration, 182, and passes to the interior washing basin, 112, via an optional, internally sealed penetration, 183. The multi-channeled tube, 181, is comprised of at least two channels which allow fluids to travel in either direction. The intake channel, 189, pulls in-coming rinsing or washing water, 148, from the wash basin, 112, to the pump (not shown) of the electrochemical device, 180, wherein the washing water, 148, is electrolyzed and pumped or discharged back to the wash basin, 112 via the discharge channel, 190, to the multi-channeled tube outlet, 184, to allow treatment of the tableware in the automatic dishwashing appliance, 100, via the normal wash and/or rinse cycles.

The optional penetrations may be in the body of the automatic dishwashing appliance, 100, or in the closeable door (not shown). As an alternative the multi-channeled tube, 181, may be held between the closed door (not shown) and the body (not shown) of the automatic dishwashing appliance, 100, without the need for separate penetration(s). The non-immersed, unattached electrolytic device, 180, is powered by an external power source, 186, via an electrical cord, 185, and plug, 195.

Figure 9:
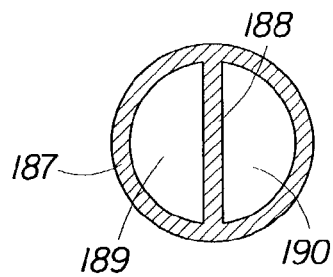
FIG. 9 shows a cross-section of the multi-channeled tube for delivery of electrolyzed water to an automatic dishwashing appliance from a non-immersed, unattached electrolytic device powered by an external power source.

FIG. 9 shows a cross-section of the multi-channeled tube, 187, comprising an intake channel, 189, for delivery of washing water to the electrolytic device, 180. The intake channel, 189, is separated from the discharge channel, 190, with an inner wall, 188. The discharge channel, 190, provides for delivery of the electrolyzed water from the electrolytic device to the wash basin of an automatic dishwashing appliance. The outside diameter of the multi-channel tube, 187, is optimized in order to provide adequate concentrations and delivery of electrolyzed wash and/or rinse liquor to the wash basin of the automatic dishwashing appliance during the wash and/or rinse cycle for the purposes of providing adequate the required stay times for proper production of bleach species in the electrochemical cell itself. The outside diameter can vary from, but is not limited to 0.125 inches to 2 inches, preferably 0.25 inches to 1 inch.

Figure 10:
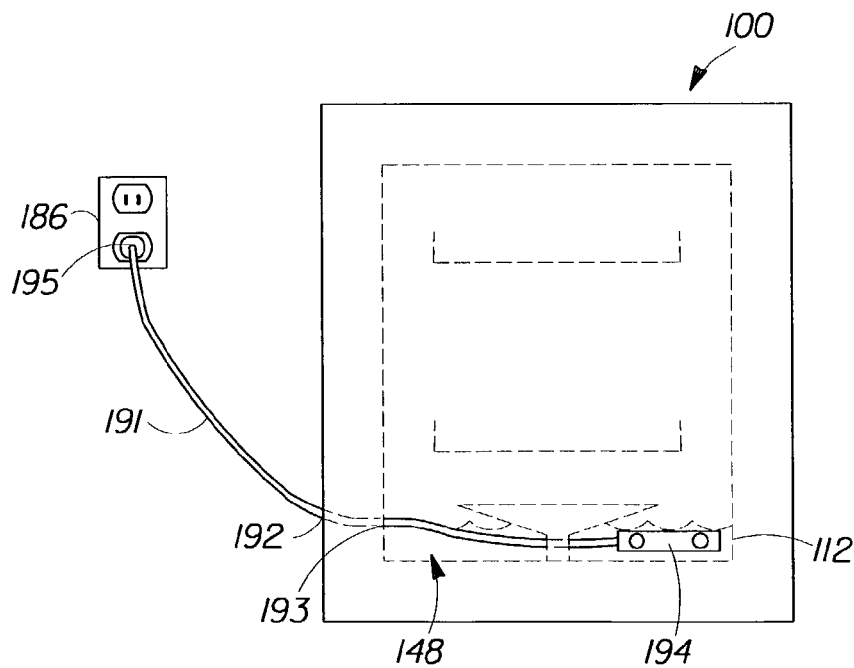
FIG. 10 shows an automatic dishwashing appliance comprising an immersed, unattached electrolytic device powered by an external power source.

FIG. 10 shows an automatic dishwashing appliance comprising an immersed, unattached electrolytic device powered by an external power source. In this embodiment the electrolytic device, 194, comprising an electrochemical cell (not shown) is physically located inside the wash basin, 112, of the automatic dishwashing appliance, 100, in fluid communication with the rinsing or washing water, 148, via immersion of the electrochemical cell (not shown) which electrolyzes at least some of the washing water, 148, in the wash basin, 112, to allow treatment of the tableware in the automatic dishwashing appliance, 100, via the normal wash and/or rinse cycles. The immersed, unattached electrolytic device, 194, may be selected from, but is not limited to, any of the immersed, unattached electrolytic devices described herein.

The device is suitably insulated and constructed to insure safety and avoid leakage. The immersed, unattached electrolytic device, 194, is powered by an external power source, 186, via an electrical cord, 191, and plug, 195. The electrical cord, 191, enters the exterior body (not numbered) of the automatic dishwashing appliance, 100, via an optional, externally sealed penetration, 192, and passes to the interior washing basin, 112, via an optional, internally sealed penetration, 193. The optional penetrations may be in the body of the automatic dishwashing appliance, 100, or in the closeable door (not shown). As an alternative, the electric cord, 191, may be held between the closed door (not shown) and the body (not shown) of the automatic dishwashing appliance, 100, without the need for a separate penetration.

Electrochemical Cell

Figure 11:
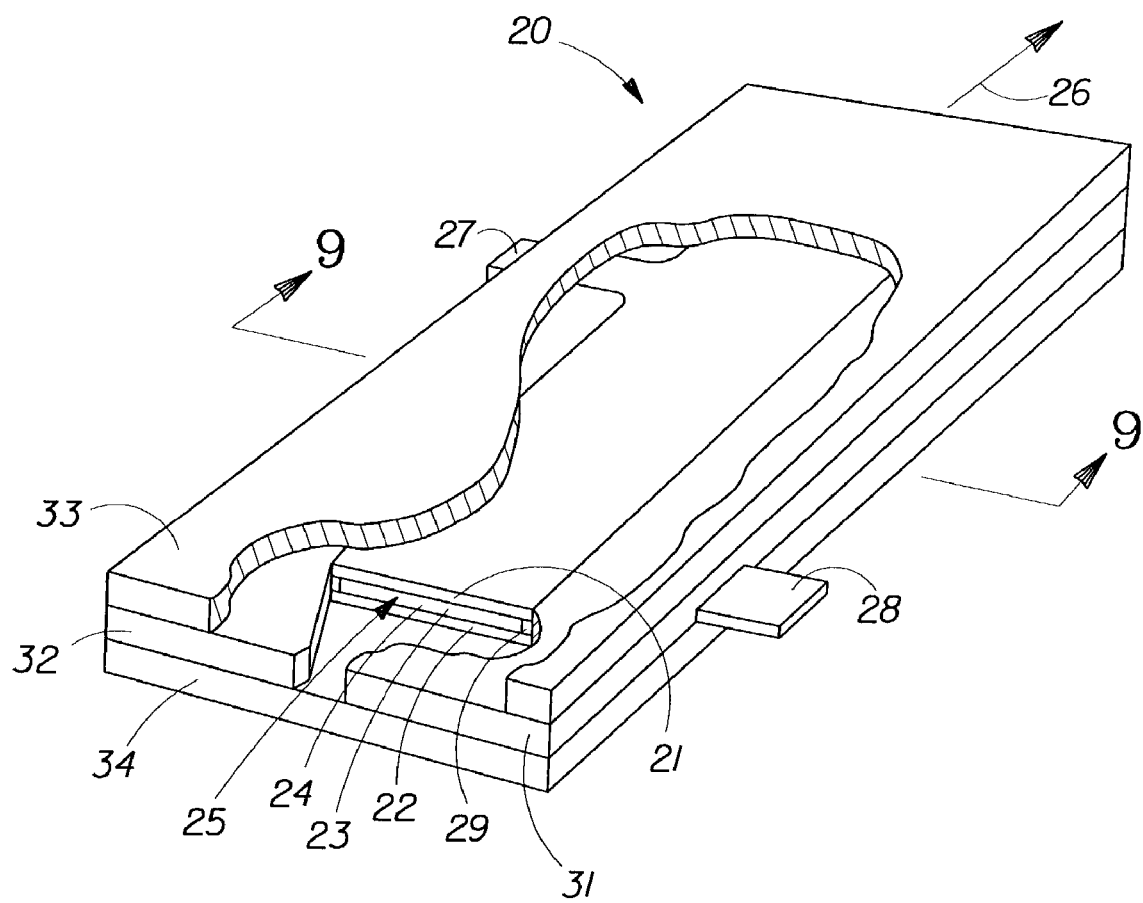
FIG. 11 shows an electrochemical cell.

One embodiment of the present invention relates to an unattached electrolytic device wherein the electrochemical cell can be non-partitioned. FIG. 11 shows an embodiment of the unattached, non-partitioned electrochemical cell, 20, of the present invention. The electrochemical cell, 20, can comprise at least one pair of electrodes; an anode, 21, and a cathode, 22, defining a cell gap, 23, comprising a cell passage, 24, formed therebetween through which said aqueous electrolytic solution can flow. The electrodes are held a fixed distance away from one another by at least one pair of opposed non-conductive electrode holders, 31, having electrode spacers, 29, that space apart the confronting longitudinal edges of the anode, 21, and cathode, 22 thereby defining the cell gap, 23, comprising the cell passage, 24. The cell passage, 24, has an inlet opening, 25, through which the aqueous electrolytic solution can pass into of the electrochemical cell, 20, and an opposed outlet opening, 26, from which the effluent can pass out of the electrochemical cell, 20.

Figure 12:
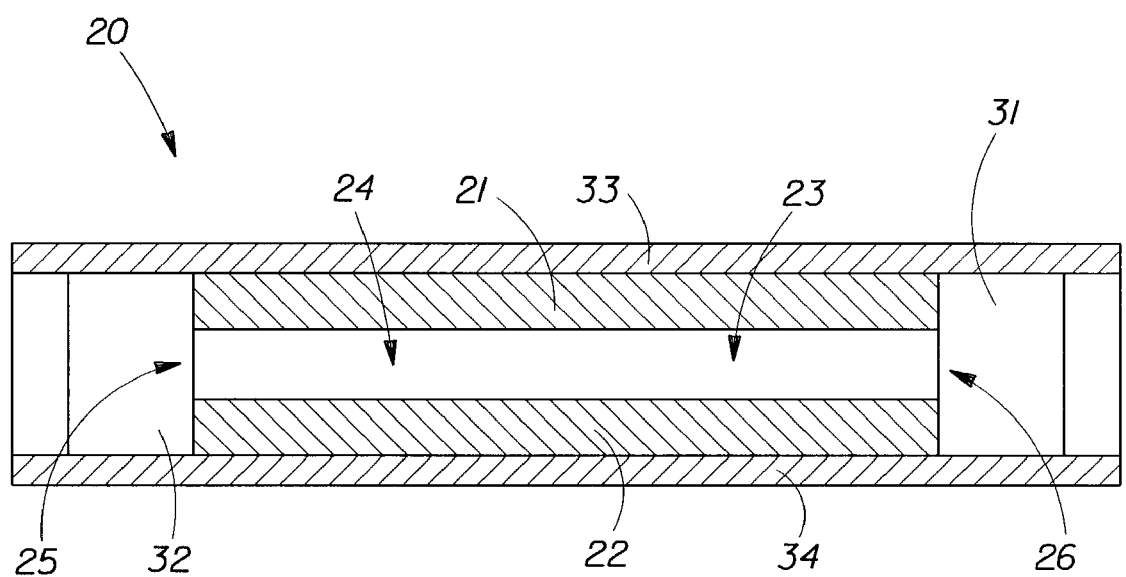
FIG. 12 shows cross-section of an electrochemical cell.

FIG. 12 shows the cross-section (2-2) of the electrode in FIG. 11. The assembly of the anode, 21, and cathode, 22, and opposed plate holders, 31, are held tightly together between a non-conductive anode cover, 33, (shown partially cut away), and cathode cover, 34, by a retaining means (not shown) that can comprise non-conductive, water-proof adhesive, bolts, or other means, thereby restricting exposure of the two electrodes only to the aqueous electrolytic solution that flows through the passage, 24. Anode lead, 27, and cathode lead, 28, extend laterally and sealably through channels made in the electrode holders, 31.

The gap, 23, between the at least one pair of electrodes has a gap spacing between about 0.1 mm to about 5.0 mm. The operating voltage that can be applied between the at least one pair of electrodes can be between about 1 and about 12 volts; preferably between about 3 volts and 6 volts. The electrochemical cell, 20, can be disposable and/or replaceable via a refill and/or a replacement cartridge which can be removable from at least one sealed or sealable compartment, 14, of the unattached, self-powered, self-contained electrolytic device. The at least one sealed or sealable compartment, 14, can be located separately and independently from other compartments located within the body, 12, of the unattached electrolytic device, 10a, 10b, 10c, 10d, or 10e (see also FIGS. 1-5).

The electrochemical cell, 20, can also comprise two or more anodes, 21, or two or more cathodes, 22. The anode, 21, and cathode, 22, plates are alternated so that the anode, 21, can be confronted by a cathode, 22, on each face, with a cell passage, 24, therebetween. Examples of electrochemical cells that can comprise a plurality of anodes and cathodes are disclosed in U.S. Pat. No. 5,534,120, issued to Ando et al. on Jul. 9, 1996, and U.S. Pat. No. 4,062,754, issued to Eibl on Dec. 13, 1977, which are incorporated herein by reference.

The electrochemical cell, 20, of FIG. 2 will generally have at least one inlet opening, 25, in fluid communication with each cell passage(s), 24, and at least one outlet opening, 26, in fluid communication with the cell passage(s), 24. The inlet opening, 25, can be also in fluid communication with the source of aqueous electrolytic solution in the washing basin (not shown) of the appliance (not shown), such that the aqueous electrolytic solution can flow into the inlet opening, 25, through the cell passage, 24, and from the outlet opening, 26, of the electrochemical cell, 20.

The discharge effluent (the electrolyzed aqueous electrolytic solution that exits from the electrochemical cell) can comprise an effective amount of halogenated mixed oxidants that was converted within the cell passage, 24, in response to the flow of electrical current through the aqueous electrolytic solution. The discharge effluent can be used as a source of halogenated mixed oxidants, for example, for sanitizing or bleaching tableware. The effluent can itself be a treated solution, where the aqueous electrolytic solution contains microorganisms or some other oxidizable source material that can be oxidized in situ by the halogenated mixed oxidants that can be formed.

Another embodiment of the present invention relates to an unattached electrolytic device comprising a robust electrochemical cell, wherein the robust cell can comprise a cathode of stainless steel and an anode of titanium, and wherein the anode can be coated and/or layered with at least one of the materials selected from the group consisting of platinum, ruthenium iridium, and oxides, alloys, and mixtures thereof. The cell passage of the robust cell forms a gap between the at least one pair of electrodes having a gap spacing between about 0.1 mm to about 0.5 mm; and wherein the operating voltage can be between about 3 and about 6 volts.

Electrodes

An electrode of the present invention can generally have any shape that can effectively conduct electricity through the aqueous electrolytic solution between itself and another electrode, and can include, but can be not limited to, a planar electrode, an annular electrode, a spring-type electrode, and a porous electrode. The anode, 21, and cathode, 22, electrodes can be shaped and positioned to provide a substantially uniform gap, 23, between a cathode, 22, and an anode, 21, electrode pair, as shown in FIG. 11.

On the other hand, the anode, 21, and the cathode, 22, can have different shapes, different dimensions, and can be positioned apart from one another in a non-uniform manner, as shown in FIG. 11 and FIG. 10. The important relationship between the anode, 21, and the cathode, 22, can be for a sufficient flow of current through the anode, 21, at an appropriate voltage to promote the conversion of the halogenated salt solution to halogenated mixed oxidants within the cell passage adjacent the anode, 21.

Planar electrodes, such as shown in FIG. 11, have a length along the flow path of the solution, and a width oriented transverse to the flow path. The aspect ratio of planar electrodes, defined by the ratio of the length to the width, can be generally between 0.2 and 10, more preferably between 0.1 and 6, and most preferably between 2 and 4.

The electrodes, both the anode, 21, and the cathode, 22, are commonly metallic, conductive materials, though non-metallic conducting materials, such as carbon, can also be used. The materials of the anode, 21, and the cathode, 22, can be the same, but can advantageously be different. To minimize corrosion, chemical resistant metals are preferably used. Examples of suitable electrodes are disclosed in U.S. Pat. Nos. 3,632,498 and 3,771,385. Preferred anode metals are stainless steel, platinum, palladium, iridium, ruthenium, as well as iron, nickel and chromium, and alloys and metal oxides thereof. More preferred are electrodes made of titanium, tantalum, aluminum, zirconium, tungsten, alloys thereof, and mixtures thereof, which are coated or layered with a Group VIII metal that can be preferably selected from platinum, iridium, and ruthenium, and oxides and alloys thereof. One preferred anode, 21, can be made of titanium core and coated with, or layered with, ruthenium, ruthenium oxide, iridium, iridium oxide, and mixtures thereof, having a thickness of at least 0.1 micron, preferably at least 0.3 micron.

For many applications, a metal foil having a thickness of about 0.03 mm to about 0.3 mm can be used. Foil electrodes should be made dimensionally stable in the electrochemical cell so that they do not warp or flex in response to the flow of liquids through the passage that can interfere with proper electrolysis operation. The use of foil electrodes can be particularly advantageous when the cost of the device should be minimized, or when the lifespan of the electrolysis device can be expected or intended to be short, generally about one year or less. Foil electrodes can be made of any of the metals described above, and are preferably attached as a laminate to a less electrically-conductive base metal, such as tantalum, stainless steel, and others.

Figure 13:
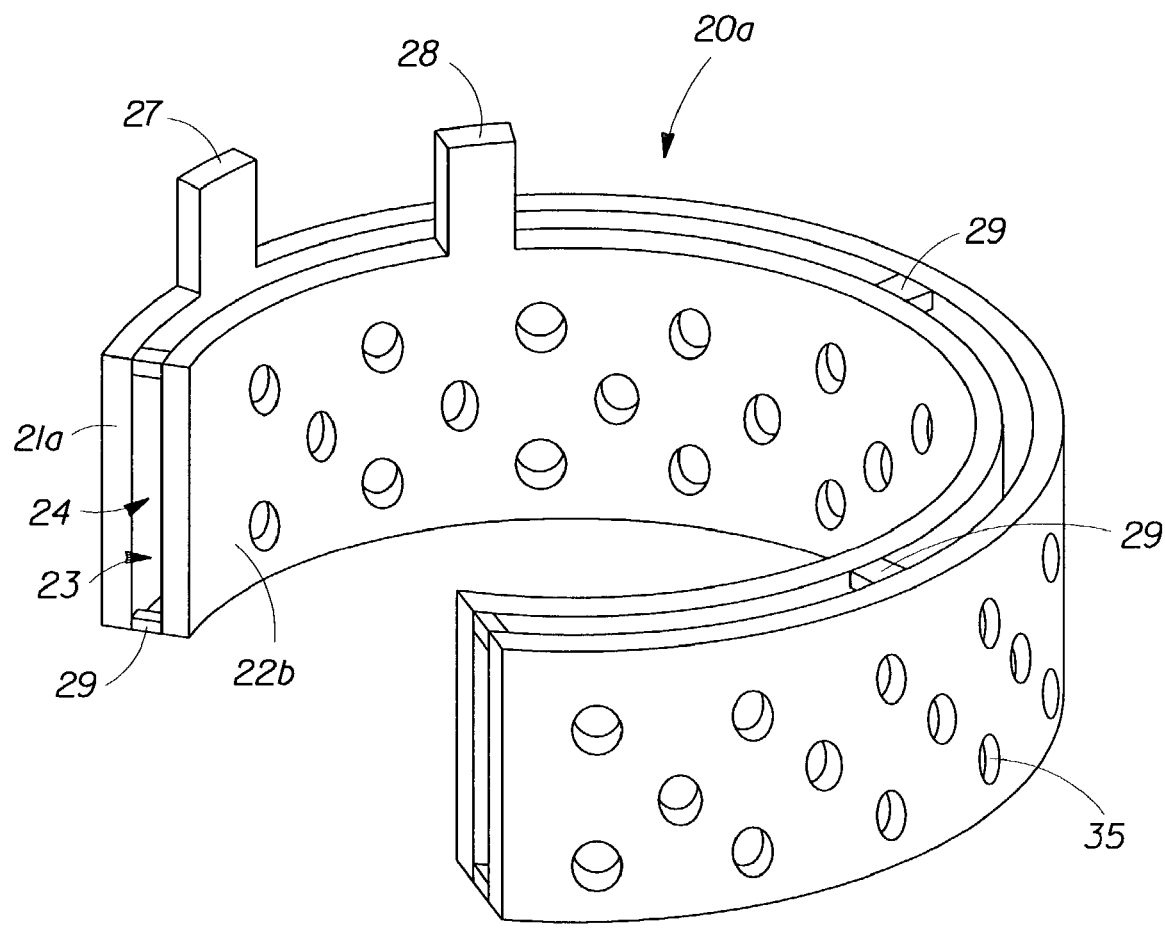
FIG. 13 shows annular electrochemical cell.

FIG. 13 shows a particularly preferred anode electrode of the present inventions can be a porous, or flow-through anode, 21a. The porous anode, 21a, has a large surface area and large pore volume sufficient to pass there through a large volume of electrolytic solution. The plurality of pores, 35, and flow channels in the porous anode, 21a, provide a greatly increased surface area providing a plurality of passages, through which the aqueous electrolytic solution can pass. Cincinnati, Ohio, Porvair Inc. in Henderson, N.C., or Mott Metallurgical in Farmington, Conn. Alternately U.S. Pat. Nos. 5,447,774 and 5,937,641 give suitable examples of porous media processing. Preferably, the porous anode, 21a, has a ratio of surface area (in square centimeters) to total volume (in cubic centimeters) of more than about 5 $cm^{-1}$, more preferably of more than about 10 $cm^{-1}$, even more preferably more than about 50 $cm^{-1}$, and most preferably of more than about 200 $cm^{-1}$. Preferably the porous anode, 21a, has a porosity of at least about 10%, more preferably of about 30% to about 98%, and most preferably of about 40% to about 70%. Preferably, the porous anode, 21a, has a combination of high surface area and electrical conductivity across the entire volume of the anode, to optimize the solution flow rate through the anode, and the conversion of halogenated salt solution contained in the solution to the halogenated mixed oxidants.

The flow path of the aqueous electrolytic solution through a porous anode, 21a, should be sufficient, in terms of the exposure time of the solution to the surface of the anode, 21a, to convert the halogenated electrolytic solution containing salt to the halogenated mixed oxidants. The flow path can be selected to pass the aqueous electrolytic solution in parallel with the flow of electricity through the porous anode (in either the same direction or in the opposite direction to the flow of electricity), or in a cross direction with the flow of electricity. The porous anode, 21a, permits a larger portion of the aqueous electrolytic solution to pass through the passages adjacent to the anode surface, thereby increasing the proportion of the halogenated salt solution that can be converted to the halogenated mixed oxidants.

One embodiment of the present invention relates to an unattached electrolytic device which comprises an electrochemical cell with a cell gap between the at least one pair of electrodes having a gap spacing between about 0.1 mm to about 5.0 mm; and wherein the operating voltage can be between about 1 and about 12 volts.

Electrolytic Solution

The components of the aqueous electrolytic solution can be selected from the group consisting of chloride ions, chlorite ions, water-soluble salts having the formula $(M)_x(XO_2)_y$ and/or $(M)_x(X)_y$ wherein X can be Cl, Br, or I and wherein M can be a metal ion or cationic entity and wherein x and y are chosen such that said salt can be charge balanced, electrolysis precursor compounds, electrolysis precursor salts with low water solubility, electrolysis precursor compounds contained within a medium or matrix for controlled release, and mixtures thereof.

Preferred electrolytic solutions contain at least some halogen ions, including but not limited to chloride, chlorite, bromide, bromite, iodide, and iodite, and mixtures thereof, preferably chloride ions or chlorite ions. Of course, electrolytic solutions containing higher levels of halogen ions are more efficiently converted into a discharge effluent solution having even larger amounts of the mixed oxidants. This can be due in part because the conductivity of the aqueous electrolytic solution increases with the concentration of halogen ions, thereby enabling a greater current flow across the passage gap between the pair of electrodes under a constant voltage potential. In general, to produce the same amount of mixed oxidants at a fixed power (current and voltage potential), an aqueous electrolytic solution having a higher concentration of halogen ions allows substantially smaller gap spacing, compared to an aqueous electrolytic solution having lower concentrations of the halogen ions.

Preferably the aqueous electrolytic solution has a specific conductivity ρ of greater than 100 μS/cm, preferably more than 150 μS/cm, even more preferably more than 250 μS/cm, and most preferably more than 500 μS/cm.

Electrical Current Supply

Another embodiment of the present invention relates to an unattached electrolytic device comprising a source of electrical current supply, wherein one or more electrical batteries can supply the current. The electrical battery can be preferably rechargeable. The unattached electrolytic device can further comprise at least one sealed or sealable compartment wherein the battery can be integrated within the unattached electrolytic device via the at least one sealed or sealable compartment.

An electrical current supply provides a flow of electrical current between the electrodes and across the passage of aqueous feed solution passing across the anode. A preferred electrical current supply can be a battery or set of batteries, preferably selected from an alkaline, lithium, silver oxide, manganese oxide, or carbon zinc battery. The batteries can have a nominal voltage potential of 1.5 volts, 3 volts, 4.5 volts, 6 volts, or any other voltage that meets the power requirements of the electrolysis device. Most preferred are common-type batteries such as "AA" size, "AAA" size, "C" size, and "D" size batteries having a voltage potential of 1.5 V. Two or more batteries can be wired in series (to add their voltage potentials) or in parallel (to add their current capacities), or both (to increase both the potential and the current). Re-chargeable batteries and mechanical wound-spring devices can also be advantageously employed and can be integrated within body of the device via at least one sealed or sealable compartment.

An alternative electrical current supply is a rectifier of household (commercial or industrial) current that converts common 100-230 volt AC current to DC current. Another alternative is a solar cell that can convert (and store) solar power into electrical power. Solar-powered photovoltaic panels can be used advantageously when the power requirements of the electrochemical cell draws currents below 2000 milliamps across voltage potentials between 1.5 and 9 volts. In another embodiment of the present invention, the electrical current supply can come from building electrical current supply via the electrical outlet. The device can comprise a rectifier of household (commercial or industrial) current that converts common 100-230 volt AC current to DC current via a cord and plug.

One embodiment of the present invention can be an unattached, self-powered, self-contained electrolytic device comprising an electrochemical cell that can use the current and voltage delivered by conventional household batteries. The electrochemical cells can come in various sizes, with anodes having a surface area of from about 0.1 cm² to about 60 cm². In one embodiment, the electrochemical cell can comprise at least one single pair of electrodes having the anode connected to the positive lead and the cathode connected to the negative lead of the battery or batteries. A series of two or more electrodes, or two or more cells (each a pair of electrodes) can be wired to the electrical current source, 30. Arranging the electrochemical cells in parallel, by connecting each cell anode to the positive terminal(s) and each cell cathode to the negative terminal(s), provides the same electrical potential (voltage) across each cell, and divides (evenly or unevenly) the total current between the two or more electrode pairs. Arranging two cells (for example) in series, by connecting the first cell anode to the positive terminal, the first cell cathode to the second cell anode, and the second cell cathode to the negative terminal, provides the same electrical current across each cell, and divides the total voltage potential (evenly or unevenly) between the two cells.

The electrical current supply can further comprise a circuit for periodically reversing the output polarity of the battery or batteries in order to maintain a high level of electrical efficacy over time. The polarity reversal minimizes or prevents the deposit of scale and the plating of any charged chemical species onto the electrode surfaces. Polarity reversal functions particularly well when using confronting anode and cathode electrodes.

Operation of the Electrochemical Cell

The chemistry of the conversion of halogen ions to halogenated mixed oxidants proceeds as electrical energy can be applied between the pair of electrodes and through the aqueous electrolytic solution. Since chloride can be the most prevalent halogen available, the description of the electrochemical cell chemistry and operation will be described with respect to converting chloride to chlorine, although it should be understood that other halides or halites, especially bromide, iodide, chlorite, bromite, and iodite would function and respond similarly to chloride. Similarly, since chlorinated tap water can be a particularly preferred electrolytic solution, the description below will describe the use of water having a residual amount of chloride ions, although it should be understood that other electrolytic solutions can be used, preferably those consisting of chloride ions, chlorite ions, water-soluble salts having the formula $(M)_x(XO_2)_y$ and/or $(M)_x(X)_y$ wherein X can be Cl, Br, or I and wherein M can be a metal ion or cationic entity and wherein x and y are chosen such that said salt can be charge balanced, electrolysis precursor compounds, electrolysis precursor salts with low water solubility, electrolysis precursor compounds contained within a medium or matrix for controlled release, and mixtures thereof.

Water containing residual amounts of chloride ions can be electrolyzed as it passes between the anode (the positively charged electrode of the pair) and the cathode (the negatively charged electrode). Two of the reactions that occur at the anode electrode are set forth below as equations 1 and 2.

$$2Cl^- \rightarrow Cl_2 + 2e^- \qquad (1)$$

$$H_2O \rightarrow 1/2 O_2 + 2H^+ + 2e^- \qquad (2)$$

One of the reactions that occurs at the cathode can be set forth as equation 3.

$$2H_2O + 2e^- \rightarrow H_2 + 2OH^- \qquad (3)$$

Furthermore, chlorine molecules can be converted to hypochlorous acid and hypochlorite ions as set forth in equations 4 and 5, respectively.

$$Cl_2 + H_2O \rightarrow HOCl + Cl^- + H^+ \qquad (4)$$

$$HOCl \rightarrow OCl^- + H^+ \qquad (5)$$

The chlorine gas that can be generated dissolves or diffuses into the water to generate free chlorine in the form of hypochlorous acid, hypochlorous acid ions, and hypochlorite ions. It can be believed that other various mixed oxidant species that can form include chlorine dioxide ($ClO_2$), other chloro-oxides molecules, oxide molecules including ozone, hydrogen oxide ($H_2O_2$) and free radicals (oxygen singlet, hydroxyl radicals) and ions thereof. Such mixed oxidants are demonstrated and described in U.S. Pat. Nos. 3,616,355 and 4,761,208. These types of mixed oxidants are very effective biocidal agents, but have very short lifespans, lasting from a fraction of a second to minutes under ordinary, ambient conditions. Consequently, generating these biocidal agents at the point of use ensures the most effective use of the biocidal species, such as when generating the biocidal agents at specific time intervals throughout the wash and/or rinse cycles of said appliance or continuously throughout the use of the solution in a countertop sink reservoir application.

For effective sanitizing treatment of tableware in contact with the aqueous electrolytic solution, the concentration of mixed oxidants in the electrochemical cell effluent, as measured by the DPD method, can be at least about 0.1 mg per liter (about 0.1 ppm) of electrochemical cell effluent, preferably 0.2 mg per liter (about 0.2 ppm), more preferably at least 1 mg per liter (about 1 ppm), and most preferably at least 5 mg per liter (about 5 ppm).

An important consideration can be the productivity of the electrical power of the device. When battery power can be used, it can be important to provide the greatest possible production of halogenated mixed oxidants or mixed oxidant agents for each watt of power consumed. This ensures long battery life, greater consumer convenience, smaller and more portable devices, and greater consumer value.

The productivity of an electrochemical cell can be expressed by equation I, $$\eta = (CCl)(Q)/(I)(V) \tag{I}$$

wherein:

$\eta$ units are micrograms of chlorine per minute, per watt of power used;

CCl can be the concentration of the generated chlorine equivalent, as determined by the DPD Method, in milligrams per liter (mg/l);

I can be the electric current in amps;

Q can be the volumetric flow rate in milliliters per minute (ml/m); and

V can be electric potential across the electrochemical cell in volts.

The productivity $\eta$ of the electroytic device used in accordance with the present invention can be typically greater than 100, and more typically greater than 250. In preferred embodiments of the electrochemical cell, the productivity $\eta$ can be more than about 500, and more preferably more than about 1000, when the aqueous electrolytic solution has a concentration of halogen ions of more than 0.001% (10 ppm) and less than about 0.1%. Preferably, the unattached electrolytic device has the above-described efficiencies when the electric current can be between about 100 milliamps and about 2000 milliamps, with typical current densities of between about 5 milliamps/cm$^2$ and 100 milliamps/cm$^2$ of exposed anode electrode surface, and more preferably between about 10 milliamps and 50 milliamps/cm$^2$. Since the electrical potentials required to convert chloride to chlorine can be about 1.36V, a voltage potential greater than 1.36V across the passage will generate a proportionally greater amount of mixed oxidants from the chloride ions. The voltage potential maintained between any pair of anode and cathode electrodes should be generally greater than 1.36V, and generally less than about 12 volts, and can be preferably between about 2.0V and 6V, and more preferably between about 3V and 4.5V. For self-powered self-contained devices, batteries are the preferred electrical current sources. To achieve the extended life from a set of batteries, the device can be preferably designed to draw a total power of 20 watts or less, preferably 5 watts or less, more preferably 2.5 watts or less, and most preferably 1 watt or less, across the electrode pairs of the electrochemical cell.

Generally, the electrochemical cell has a cell gap spacing greater than about 0.05 mm, preferably greater than 0.10 mm, more preferably greater than 0.15 mm, and most preferably greater than about 0.20 mm, and a cell gap spacing less than about 5 mm, preferably less than about 2.0 mm, more preferably less than about 0.80 mm, and most preferably less than about 0.50 mm. The more preferable cell gap spacings are for use with electrolytic solutions that contain a concentration of halide ions of less than about 200 ppm, and a specific conductivity $\rho$ of greater than about 250 µS/cm.

The residence time between the inlet and outlet of the anode and cathode pair can be generally less than about 10 seconds and preferably can be less than about 5 seconds, in more preferred embodiments, between about 0.01 seconds and about 1.5 seconds, and most preferably between 0.05 and about 0.5 seconds. The residence time can be approximated by dividing the total volume of the passage between the anode and cathode pair by the average flow rate of water through the electrochemical cell.

Operation and effectiveness of the unattached electrolytic device requires that the aqueous electrolytic solution passes through the electrochemical cell in a quantity sufficient to generate an effective production of the halogenated mixed oxidants for the intended purpose. In general, without some means of moving the aqueous electrolytic solution through the electrochemical cell, as opposed to simply filling the electrochemical cell, low levels of the halogenated mixed oxidants will be produced. Electrolytic solution comprising wash and/or rinse liquor can be moved through the unattached electrolytic device and/or electrochemical cell by pumping through the electrochemical cell via an internal and/or external pumping means, by movement of the device body through the countertop sink reservoir, such as by propulsion, or by pulling or pushing the device through the countertop sink reservoir by a tether or at the end of a handle. Alternatively, the device can be placed into an area of the appliance washing basin or countertop sink reservoir where there can be water flow sufficient to pass through the electrochemical cell by gravity flow.

Discharge Effluent

Another embodiment of the present invention relates to an unattached electrolytic device comprising wherein the discharge effluent can be released outside the device through the outlet port by means of a pump located within the unattached electrolytic device via at least one additional and separate, sealed or sealable compartment. The pump can be housed in the separate compartment within the unattached electrolytic device.

Another embodiment of the present invention relates to an unattached electrolytic device wherein the discharge effluent can be released outside the unattached electrolytic device and into the appliance through the outlet port by gravity flow.

The discharged effluent containing the electrolyzed halogenated mixed oxidants can be removed from the electrochemical cell and can be used, for example, as an aqueous sanitization or an aqueous bleaching solution. The effluent can be used as-made by direct delivery to an oxidizable source such as one that can be oxidized by the halogenated mixed oxidants. The oxidizable source can be a second source of water or other aqueous solution comprising microorganisms, which are destroyed when mixed or contacted with the effluent solution. Microorganisms present on the tableware or within the aqueous electrolytic solution would also be destroyed. The oxidizable source can also be an article or object on which oxidizable material can be affixed or positioned, such as a dishware, tableware, countertop sinks, as well as, stains on the inside surfaces of an automatic dishwashing appliance.

The concentrated effluent containing a high concentration of halogenated mixed oxidants can be achieved and maintained by holding and/or storing the effluent in glass-lined and chemically-resistant plastic surfaced containers, such as in the washing basin of an automatic dishwashing appliance.

When halogenated mixed oxidants oxidize an oxidizable material, such as a microorganism or a bleachable stain on tableware, the halogenated mixed oxidants revert back to a lower oxidation state, such as sodium chloride, sodium chlorite, and the like. Because the method and apparatus of the present invention can convert a halogen into halogenated mixed oxidants in simple, non-partitioned, electrochemical cells, a preferred system for forming halogenated mixed oxidants from an aqueous electrolytic solution can comprise a means for returning the reverted halogen salts back to the aqueous electrolytic solution, for subsequent re-conversion to halogenated mixed oxidants. This can be accomplished by recirculation.

Recirculation

One embodiment of the present invention relates to an unattached electrolytic device which comprises an electrolytic composition comprising recirculated wash and/or rinse liquor provided by the appliance, and wherein at least some of the recirculated wash and/or rinse liquor can be electrolyzed.

The aqueous electrolytic solution can comprise fresh tap water (i.e. incoming fresh water supply), recirculated wash liquor, recirculated rinse liquor, and mixtures thereof. During the wash and/or rinse cycles, the pump in the automatic dishwashing appliance continually circulates and re-circulates the aqueous electrolytic solution comprising wash and/or rinse liquor from the appliance washing basin through the self-powered, self-contained, electrolytic device comprising the electrochemical cell, comprising cell passage having an inlet opening and an outlet opening. The inlet and outlet openings are in fluid communication with the aqueous electrolytic solution comprising the wash and/or rinse liquors thus allowing release, discharge, or propulsion of at least some electrolyzed water as an effluent outside the self-powered, self-contained, recirculating electrolytic device (hereinafter "recirculating device") into the washing basin of the dishwashing appliance.

The recirculated, electrolytic solution present in the appliance can be continually available for electrolytic treatment during operation. In one embodiment, the discharge effluent being in fluid communication with the wash and/or rinse liquor can be discharged or released outside the recirculating device through the outlet port into the washing basin of the dishwashing appliance by simply gravity flow. In another embodiment, the recirculating device can further comprise an internal pumping means to propel the discharge effluent into the appliance through the outlet port. The pump of the device can be located within the at least one compartment of the body or in a separate compartment within the body of the device.

In time, the concentration of the un-reacted halogenated salt in the aqueous electrolytic solution can be reduced to a low level whereby the charged amount of the halogenated salt in the aqueous electrolytic solution will have been nearly completely converted to halogenated mixed oxidants.

The following U.S. patents disclose recirculation means and methods: U.S. Pat. Nos. 5,924,432; 5,868,937; 5,837,151; 4,392,891; 4,098,616; 3,698,407; and 3,807,419.

Feed Means

The means for passing the aqueous electrolytic solution (herein after, "feed means") into the electrochemical cell can be a pump, or an arrangement where gravity or pressure forces aqueous electrolytic solution into the electrochemical cell. The means for delivering the aqueous effluent into contact with the halogen depletion target can be the feed means, or can be a separate pump or gravity/pressure arrangement.

The system can also comprise a re-circulation line through which at least some of the effluent solution can be returned back to the inlet of the electrochemical cell. As herein before described, re-circulating the effluent back to the electrochemical cell increases the total conversion of the halogenated salt solution to the halogenated mixed oxidants.

The means for returning the depleted effluent can be a collection tank with a means, such as any of the feed means, for recycling the depleted effluent back to the source.

The following U.S. patents disclose feed means, pumps and methods: U.S. Pat. Nos. 6,182,674; 5,909,743; 5,848,601; 5,711,325; 5,803,100; 5,450,868; 5,377,707; 5,143,513; 4,753,570.

Pumping Means

The device can be provided with a pump means for pumping the aqueous electrolytic solution through the cell passage. The pumping means can provide three functions: to move electrolytic solution from the automatic dishwashing appliance washing basin or countertop sink reservoir through the electrochemical cell, where halogenated mixed oxidants can be generated from halogen ions when electric current can be passed through the electrochemical cell; to expel and disperse the effluent solution, containing the halogenated mixed oxidants, back into the automatic dishwashing appliance washing basin or countertop sink reservoir; and to provide movement (propulsion) of the device through the countertop sink reservoir in response to the force of the effluent solution leaving the device.

A preferred pumping means can comprise a pump having a rotating impeller, mounted inside the body, and having a pump inlet in fluid communication with the aqueous electrolytic solution comprising wash and/or rinse liquor, and a pump outlet in fluid communication with the inlet of the electrochemical cell. The pump can be housed in a separate compartment within self-powered, self-contained, recirculating electrolytic device. Self-priming pumps, such as peristalsis pumps, can be used. The pump can be preferably driven by an electric, direct drive motor that can be powered by a battery, although other power means to drive the pump, such as mechanical wind-up springs or photovoltaic panels can be used. Preferably, the pump electric motor draws power of the same voltage potential as the electrochemical cell. The discharge effluent can be released, discharged or propelled outside the device through the outlet of the electrochemical cell and/or the unattached electrolytic device by means of a pump located within self-powered, self-contained, recirculating electrolytic device.

The pump can have a throughput of between 0.05 liters solution per minute, up to about 10 liters per minute. Higher pumping rates are possible, depending upon the size of the buoyant device, and the capacity of any electric current supply. For devices that are easily portable and powered by conventional alkaline batteries, a preferred pumping capacity can be between 0.1 and 5 liters per minute, and more preferably between 0.2 and 2 liters per minute.

Alternatively, an electrolytic device can comprise a pumping means which discharges through the electrochemical cell, with at least some of the discharged effluent from the electrochemical cell being recirculated back to the inlet of the pump, to provide a continuous recycle of at least some of the effluent back through the inlet of the electrochemical cell. This arrangement can increase the concentration of the resulting mixed oxides in the effluent discharged from the electrochemical cell.

The following U.S. patents disclose pumping means and regeneration methods: U.S. Pat. Nos. 6,182,674; 5,909,743; 5,848,601; 5,711,325; 5,803,100; 5,450,868; 5,377,707; 5,143,513; and 4,753,570.

Means for Activating and/or Deactivating the Electrochemical Cell

Another embodiment of the present invention relates to an unattached electrolytic device comprising a means for activating and/or deactivating the electrochemical cell at specific time intervals throughout the wash and/or rinse cycles of the appliance. For example, the means of activation and/or deactivation of the electrochemical cell can comprise a timer, sensor, and combinations thereof, and/or other means. Said sensor can be capable of analyzing or detecting the composition of the fluid or gaseous environment of the unattached electrolytic device or within the appliance, and signaling the unattached electrolytic device to activate or deactivate the electrochemical cell. When the sensor detects a volatile compound or gas selected from the group consisting of perfumes, perfume raw materials, volatile organic compounds, gases comprising oxides of carbon, sulfur, or nitrogen, and mixtures thereof, in the fluid or gaseous environment of the unattached electrolytic device or within the appliance, the sensor electrically signals the unattached electrolytic device and/or the electrochemical cell to activate or deactivate the electrochemical cell.

At specific time intervals throughout the wash and/or rinse cycles of the appliance, the portable electrolytic device can comprise at least one timer capable of turning the device on or off so as to result in optimal performance, for example to turn the device on during the middle or near the end of the wash cycle, or during one of more of the rinse cycles.

In addition, the device can comprise at least one sensor capable of analyzing or detecting the composition of the fluid or gaseous environment of the unattached electrolytic device or within the appliance. The sensor can be capable of detecting volatile compounds or gases selected from the group consisting of perfumes, perfume raw materials, volatile organic compounds, gases comprising oxides of carbon, sulfur, or nitrogen, and mixtures thereof. The sensor can also be capable of signaling the portable electrolytic device in order to activate or deactivate the operation of the electrochemical cell and/or corresponding production of halogenated mixed oxidants. When an electric signal can be sent from the sensor, the recirculating device will activate or deactivate the production of halogenated mixed oxidants. The operation of the electrochemical cell can be activated or deactivated at any specific time during the operation of the appliance, during a specific cycle (such as during the wash and/or rinse cycle), or for any other need identified by the consumer.

The following U.S. patents disclose sensors, sensing devices and methods: U.S. Pat. Nos. 5,037,615, 5,308,771, 6,051,437, 6,077,712, 6,214,203, and 6,331,244.

Filtering Means

In order to minimize particulate fouling of the electrochemical cell from the flow of recirculated electrolytic solution comprising large particles through the cell passage, a filter, removably housed in or attached to the body of the unattached electrolytic device, can be used. The filter can be made disposable and/or replaceable via a product refill and/or replacement cartridge. The filter can be located within a separate compartment of the unattached electrolytic device, incorporated within or attached to the housing of the device, or by any other means such that the filter prevents food debris and particles greater than about 0.1 mm, preferably greater than about 0.05 mm, most preferably greater than about 0.01 mm in size from entering the inlet port of the unattached electrolytic device or the inlet opening of the electrochemical cell and thereby interrupting the fluid communication of the unattached electrolytic device and the recirculating electrolytic solution comprising wash and/or rinse liquors and ultimately preventing production of new halogenated mixed oxidants.

Another embodiment of the present invention relates to an unattached electrolytic device comprising a filtering means to minimize fouling of the electrochemical cell from the flow of the recirculated electrolytic solution through the cell passage. The filtering means can comprise a filter removably housed in or attached to the body. The filter can be disposable and/or replaceable.

The shape or form of the filter will not be described as it can take on any shape or form. The filter itself can be comprised of any number available materials generally used in the art. These include, but are not limited to, plastic, metal, wire mesh, cloth, paper, and composites. The filter housing containing the actual filter can be made of plastic, metal, cloth, paper, and composites.

The filter can be self-cleaning, comprising a cleaning means, for example, a reversible pump to reverse the flow through the device and discharge the effluent out the inlet port, a sprayer attached to a clean water source to spray clean the filter, or any other means for cleaning the filter.

The following U.S. patents disclose filters, filtering devices, and methods: U.S. Pat. Nos. 6,234,184; 6,182,674; 5,909,743; 5,345,957; 4,038,103; 5,711,326; 5,601,660; 4,998,548; 4,468,333; and 3,575,185.

Regeneration Means

Another embodiment of the present invention relates to an unattached electrolytic device comprising a cell regeneration means to extend the operating life of the at least one pair of electrodes by descaling or unfouling the at least one pair of electrodes. The electrochemical cell regeneration means can comprise a liquid electrode cleansing composition, which can be periodically flushed through the cell passage of the electrochemical cell.

Electrochemical cell regeneration can be required to extend the operating life of the at least one pair of electrodes of the present invention when the electrodes are impacted by an electrolytic composition comprising hard water, large particulates and/or debris, or other contaminants that are capable of reducing the efficiency of the process of electrolysis of water within the unattached electrolytic device and/or electrochemical cell. In order to produce effective levels of halogenated mixed oxidants, oxidants and/or mixed oxidants, periodic or continuous addition of an electrode cleansing composition through the electrochemical cell passage can be required to maintain adequate electrical efficacy of the electrodes over time and corresponding satisfactory operation of the electrochemical cell itself.

The liquid electrode cleansing composition can be selected from the group consisting of an anticorrosion agent, descaling agent, and mixtures thereof. Common household vinegar can be an example of an anticorrosion agent or descaling agent.

Another means for cell regeneration involves polarity reversal of the battery or batteries to minimize or prevent the deposit of scale and the plating of any changed chemical species onto the electrode surfaces. The electrical current supply can further comprise a circuit for periodically reversing the output polarity of the battery or batteries in order to maintain a high level of electrical efficacy over time.

The following U.S. patents disclose electrochemical cell regeneration means and methods: U.S. Pat. Nos. 5,954,939; 4,434,629; 5,932,171; JP Application No. 10057297A; and WO Patent Number 00/64325.

Local Source of Halogen Ion

An optional embodiment of the present invention includes an electrolytic device comprising a local source of halogen ions, and a means for delivering the local source of halogen ions to at least some of the aqueous electrolytic solution in fluid communication with the inlet opening. This embodiment can be advantageously used in those situations when the aqueous electrolytic solution has a very low concentration, or even no, halogen ions, thereby increasing the production of halogenated mixed oxidants in the effluent as compared to the production of halogenated mixed oxidants from the automatic dishwashing appliance washing basin or countertop sink reservoir solution alone. Preferably, the local source of halogen ion passes through the electrochemical cell, to maximize the conversion of the local source of halogen ion to halogenated mixed oxidants, and to limit adding salts to the aqueous electrolytic solution generally. The local source of halogen ions can supplement the ordinary levels of halogen ion in many water sources, such as tap water, to generate extraordinarily high concentrations of halogenated mixed oxidants in the effluent.

The local source of halogen ions can be from a detergent and/or rinse aid composition, a concentrated brine solution, a halogenated salt tablet, granule, or pellet in fluid contact with the aqueous electrolytic solution, or in a porous basket hanging on the rack of the automatic dishwashing appliance, or both. A preferred localized source of halogen ions can be a solid form, such as a pill or tablet, of halide salt, such as sodium chloride (common salt) or sodium chlorite. The means for delivering the local source of halogen ions can comprise a salt chamber or a porous basket comprising the halogenated salt, preferably a pill of tablet, through which at least some of the aqueous electrolytic solution will pass, thereby dissolving at least some of the halide salt into the portion of water. The salted portion of water then ultimately passes into the electrochemical cell. The salt chamber or a porous basket can comprise a salt void that can be formed in the body and positioned in fluid communication with the portion of water that will pass through the electrochemical cell.

A brine solution can be provided within a brine chamber that can be position in fluid communication with the inlet port of the electrochemical cell via a tube, such that a flow of brine solution will be induced through the tube by venturi suction in response to the flow of water through the inlet port, whereby a constant proportion of brine solution can be delivered. Other halogen salts with a substantially lower solubility in water can be advantageously used to control the rate of dissolution of halogenated salt. Preferred salts for use as a solid form of the local source of halogen ion are the less soluble salts, such as calcium chloride, magnesium chloride, calcium chlorite, magnesium chlorite,. The pill can also be formulated with other organic and inorganic materials to control the rate of dissolution of the sodium chloride or sodium chlorite. Preferred can be a slow dissolving salt tablet, to release sufficient halogen ions to effect the conversion of an effective amount of halogenated mixed oxidants, oxidants, and/or mixed oxidant agents. The release rate halogen ion can be typically between 0.01 to 0.3 mg halogen ion for each liter of electrolytic solution treated. The halogenated pill can be a simple admixture of the salt with the dissolution restricting materials, which can be selected from various well-known encapsulating materials.

Storage and Dispensing Means

Another embodiment of the present invention relates to an unattached electrolytic device comprising a storage means for storing at least one product prior to its release. The storage means can comprise at least one sealed or sealable compartment in the unattached electrolytic device for containing the at least one product, such that the at least one product can be released in conjunction with at least one predetermined point in time during the wash and/or rinse cycle of the appliance, wherein the at least one sealed or sealable compartment can house at least one product in the form selected from the group consisting of a tablet, free-flowing gel, free-flowing powder, free-flowing liquid, or combinations thereof, and wherein the at least one compartment can be recloseable or resealable such that the compartment's contents are not contaminated by an external medium. The storage means that ensures that the compartment's contents are not contaminated by an external medium can be achieved via a one-way valve, which allows products to flow outside but avoids contamination of the interior of the compartment from an outside medium.

Another embodiment of the present invention can comprise a storage means for containing the at least one product in at least one sealed or sealable compartment or additional compartments located within the recirculating device for discharge of the at least one product into the wash and/or rinse liquor of the appliance, the aqueous electrolytic solution, or mixtures thereof. The at least one sealed or sealable compartment will house the at least one product via a recloseable means such that the compartment's contents are not contaminated by an external medium (such as by the wash and/or rinse liquor). The storage means will allow the storage of at least one product prior to its release at specific intervals or time periods through the wash and/or rinse cycles. The dispensing or release of the at least one product can also be in conjunction with at least one predetermined point in time during the wash and/or rinse cycle of the appliance.

The reclosable means serves to prevent liquid, such as the wash /and/or rinse liquor, tap water, or electrolytic solution, from entering and contaminating the at least one product or products, and also ensures proper buoyancy according to the design criteria. The form of product or additional product selected can be a tablet, free-flowing gel, free-flowing powder, free-flowing liquid, or combinations thereof. A product refill or replacement cartridge can be provided to allow placement of the at least one product or products in the sealed or sealable compartment via an article of manufacture.

The at least one product can also be exist in direct fluid contact with wash and/or rinse liquors, tap water or electrolytic solution for at least some period of time during operation of the appliance rather contained within the sealed or sealable at least one compartment.

The product or products housed in the sealed or sealable at least one compartment or compartments can be selected from the group consisting of chloride ions, chlorite ions, water-soluble salts having the formula $(M)_x(XO_2)_y$ and/or $(M)_x(X)_y$, wherein X can be Cl, Br, or I and wherein M can be a metal ion or cationic entity and wherein x and y are chosen such that said salt can be charge balanced, electrolysis precursor compounds, electrolysis precursor salts with low water solubility, electrolysis precursor compounds contained within a medium or matrix for controlled release, electrolyzed water, detergent compositions, rinse aid compositions, electrode cleaning agents, bleach-scavenging agents, metal-protecting agents, adjunct ingredients, and mixtures thereof.

The at least one product comprising electrolytic solution can also be selected from the group consisting of a solid electrolysis precursor compound, electrolysis precursor compound matrix of low water solubility, electrolysis precursor compound with a controlled release matrix, and mixtures thereof.

When the electrolysis can be no longer desired, the at least one product can comprise a bleach-scavenging agent or a metal-protecting agent. Bleach-scavenging agents or metal-protecting agents can be selected from the group consisting of perborate, percarbonate, ascorbic acid or derivatives thereof, carbamate, ammonium, sulfite, bisulfite, aluminum tristearate, sodium silicate, benzotriazole, amines, amino acids, and mixtures thereof.

Suitable examples of storage and dispensing means, storage devices, and methods of using storage means include, but are not limited to, those found in the following: U.S. Pat. Nos. 6,338,351; 6,058,946; 5,839,454; 4,800,906; 3,827,600; and 3,612,074.

Communication Means

Another embodiment of the present invention relates to an unattached electrolytic device comprising a means for communicating to the consumer when it can be time to refill or replace the electrochemical cell cartridge. The communication means can comprise an indicator and optionally a timer and/or sensor for communicating to the consumer when it can be time to refill or replace the electrochemical cell cartridge.

Suitable examples of communication means, communication devices, and methods of using communicating include, but are not limited to, those found in the following: U.S. Pat. Nos. 6,295,004; 6,196,239; 5,839,458; 5,151,884; 4,653,423; 4,213,338; 4,164,197; 3,648,931; and 3,850,185.

Elastomeric Slit Value

One means to ensure that the compartment's contents are not contaminated by an external medium can be achieved by a one-way valve. The one-way value allows products to flow outside the device but avoids contamination of the interior of the device's compartment from an outside medium. A non-limiting example of the one-way valve can be a disposable and/or replaceable elastomeric slit valve.

If desired, a means for communicating to the consumer when it can be time to refill or replace the electrochemical cell cartridge can also be included. The communication means can comprise an indicator for communicating to the consumer when it can be time to refill or replace the electrochemical cell cartridge using a product refill or replacement cartridge.

Suitable examples of Elastomeric Slit Valves and methods of using one-way valves include, but are not limited to, those found in the following: U.S. Pat. Nos. 5,360,198; 4,870,986; 4,824,075; 4,819,691; 4,694,847; 4,193,417; 4,185,654; and 4,151,979.

A Sprayer Device

Another embodiment of the present invention relates to an unattached electrolytic device comprising a sprayer device, wherein the sprayer device can be suitable for sanitization purposes under conditions selected from the group consisting of hand dishwashing, dish pretreatment, dish post-treatment, and combinations thereof.

When performing hand dishwashing, tableware pretreatment, tableware post-treatment, and combinations thereof, a sprayer device according to this invention can be used for sanitization purposes. The sprayer device can be incorporated either within or removably attached to the automatic dishwashing appliance or electrolytic device in a manner which can be suitable for sanitization purposes in hand dishwashing, tableware pretreatment, tableware post-treatment applications. The sprayer device can be used within the appliance, in the countertop sink, in the countertop sink reservoir, and combinations thereof. The sprayer device can be immersible and provide a force sufficient to clean as well as sanitize tableware as well.

Suitable examples of sprayer devices include, but are not limited to, those found in the following: U.S. Pat. Nos. 6,357, 460; 5,954,073; 5,842,492; 4,800,906; 4,420,005; 3,903,911; and 3,809,106.

Commercial Application

The wash/rinse/dry process in a commercial automatic dishwashing appliance is typically 2 to 5 minutes long (average is around 2.5 minutes). In fact, the water temperature in a commercial appliance may be as high as 60-70 degrees C. during the wash and/or rinse cycle. Electrochemical cells and/or electrolytic devices of the present invention allow for disinfectancy of tableware during the wash and/or rinse cycle(s) of commercial appliances without the need for high temperatures or the addition of dangerous chemicals, like hypochlorite. In fact, disinfectancy can be achieved by the present invention without adding additional heat, such as at water temperatures below 48 degrees C. In addition, during a wash and/or rinse cycle with an average process time of about 2.5 minutes, the present invention may comprise a high throughput electrochemical cell and/or device (or set of devices) in order to achieve the required disinfectancy without the need to use hypochlorite. Alternatively, the electrochemical cell and/or device may also be used to control, at any selected level, the microbiological contamination of the water in a commercial automatic dishwashing appliance, especially for conveyor-low-temperature type, cabinet-low-temperature type, and combinations thereof. Thus, the commercial appliance may use water temperatures ranging from cold tap water to heated wash and/or rinse liquor up to about 70 degrees C. to reduce microbial contamination. Using electrolyzed water in the present invention reduces odors caused by the use of hypochlorite while at the same time generating low-temperature active anti-microbials in the form of halogenated mixed oxidants. The benefit results from preventing bad smell in the kitchen area, especially useful in restaurants and bars.

Furthermore, the disinfection of other types of water storage systems in commercial applications could be also accomplished with the present invention without the need of high temperature and/or hypochlorite addition.

It is generally not convenient to "retrofit" an existing dishwasher with an electrochemical device other than a self-contained, battery-powered device. For example, devices that need to be "plugged in" to the home or institution's electrical current supply (typically alternating current) are generally less convenient than simply inserting a battery-powered device into the wash or rinse water bath or elsewhere in the dishwater for wash/rinse water treatment. Nonetheless, there are some cases where it is highly advantageous to use 'retrofit' existing appliances with electrochemical devices that are not battery-powered, but that may be plugged into a suitable electrical outlet in the home or institution.

For example, in certain commercial kitchens where it is not feasible or economical to replace the existing dishwasher with a new appliance containing an attached integrated electrochemical device, it would be desirable to "retrofit" the dishwasher with a plug-in device. Because such dishwashers often involve high-throughput of dishwashing and/or heavy or continuous use, a battery-powered cell may not be preferred, and instead one would simply use a more or less self-contained electrochemical device that included a power cord and plug for connection to one of the institution's electrical outlets. The strong power of such cells would also be advantageous as commercial dishwashers sometimes have more rigorous requirements for higher levels of bleaching species. In certain homes having heavy wash loads, these devices could also find valuable use. In one embodiment of such a device, the operator might plug it in and then place the cell directly into the rinse bath of the dishwasher; the device and its power cord are suitably insulated from water. The device would have an on/off switch, located for example along the cord for convenient access. To note, the device does not draw any power from the dishwasher appliance itself. Such devices reap the advantages of a strong and continuous electrical current while avoiding the inconvenience of having to modify the electrical circuitry of the actual dishwasher appliance.

Methods of Use

Another embodiment of the present invention relates to a method for treating tableware in an automatic dishwashing appliance for improved cleaning, sanitizing, and/or stain removal comprising an unattached electrolytic device for producing electrolyzed water, said method comprising the steps of: (a) placing tableware in need of treatment into said appliance; (b) optionally providing an anti-foaming agent; (c) providing said unattached electrolytic device comprising a body comprising at least one inlet port for collecting an aqueous electrolytic solution provided by said appliance, an electrochemical cell comprising at least one inlet opening and one outlet opening, and at least one pair of electrodes defining a cell gap comprising a cell passage formed therebetween through which said aqueous electrolytic solution can flow, and a source of electrical current supply for providing electrical current between said pair of electrodes; (d) providing said aqueous electrolytic solution in fluid communication with said electrochemical cell via said inlet port of said body of said unattached electrolytic device; (e) operating said cell and/or device so that said electrochemical cell produces at least some electrolyzed water; (f) discharging said electrolyzed water into the washing basin of said appliance via said outlet opening of said cell; and (g) contacting said tableware in need of treatment with said electrolyzed water comprising wash and/or rinse liquor.

Another embodiment of the present invention relates to a method for cleaning and sanitizing or disinfecting tableware comprising an electrolytic device comprising a recirculating system for electrolyzed water.

Another embodiment of the present invention relates to a method further can comprise at least one of steps of: (a) prior to the step of providing said unattached electrolytic device, providing a composition selected from the group consisting of detergent composition, rinse aid composition, said at least one product, and mixtures thereof; (b) prior to the step of providing said unattached electrolytic device, placing at least one product into said at least one sealed or sealable compartment of an electrolytic device for release during said rinse and/or wash cycle of said appliance and manually closing said compartment; (c) prior to the step of providing said aqueous electrolytic solution, dispensing at least one product from said at least one sealed or sealable compartment of said electrolytic device; (d) after the step of operating said cell and/or device, dispensing at least one product from said electrolytic device comprising a bleach-scavenging agent or metal protection agent; and (e) combination thereof.

Another embodiment of the present invention relates to a method wherein subsequent to the period or periods of electrolysis, or during one or more of the rinses, and after which no further electrolyzed water comes into contact with said dishes, the method further can comprise the step of dispensing said chlorine bleach-scavenging agent or metal protection agent.

Another embodiment of the present invention relates to a method for washing tableware in conjunction with a separate composition comprising a solid electrolysis precursor compound of low water solubility, an electrolysis precursor compound containing a matrix of low water solubility, and mixtures thereof, said method comprising the steps of (a) providing tableware in need of treatment, pretreatment, or post-treatment in an appliance or countertop sink comprising wash and/or rinse liquor; (b) placing said unattached electrolytic device in said appliance or said sink to enable direct contact of said unattached electrolytic device with wash and/or rinse liquor comprising said separate solid electrolysis precursor compound of low water solubility, an electrolysis precursor compound containing a matrix of low water solubility, and mixtures thereof; (c) providing an electrolytic composition comprising a compound selected from the group consisting of chloride ions, chlorite ions, water-soluble salts having the formula $(M)_x(XO_2)_y$ and/or $(M)_x(X)_y$ wherein X can be Cl, Br, or I and wherein M can be a metal ion or cationic entity and wherein x and y are chosen such that said salt can be charge balanced, and mixtures thereof; (d) operating said cell and/or device so that said electrochemical cell produces at least some electrolyzed water in at least some of said wash and/or rinse liquor; and (e) contacting said tableware with said wash and/or rinse water comprising said electrolyzed water generated from said unattached electrolytic device. Another embodiment of the present invention relates to a method wherein X can be chlorine in the formula above.

Another embodiment of the present invention relates to a method wherein said unattached electrolytic device can be an unattached, non-buoyant electrolytic device.

Another embodiment of the present invention relates to a method, wherein after the step of operating said cell and/or device, said method further comprising the steps of: (a) recirculating said wash and/or rinse liquor comprising electrolyzed water again through said unattached electrolytic device via a feed means; and (b) re-contacting said tableware again with said recirculated electrolyzed water.

Another embodiment of the present invention relates to a method for cleaning or sanitizing or disinfecting tableware in an automatic dishwashing appliance in conjunction with an unattached, recirculating electrolytic device.

The electrolyzed water that exits the unattached electrolytic device can effectively sanitize, disinfect and/or sterilize the aqueous electrolytic solution comprising tap water, wash and/or rinse liquor solution, recirculated wash and/or rinse liquor, and mixtures thereof, making the aqueous electrolytic solution useful for treating tableware by providing cleaning, stain removal and sanitization benefits in both commercial, as well as, in residential applications. The recirculating device of the present invention can be used for cleaning, stain removal and sanitizing or disinfecting tableware in an automatic dishwashing appliance and/or countertop sink reservoir.

A separate composition, such as at least one product selected from the group consisting of detergent compositions, rinse aid composition, a solid electrolysis precursor compound of low water solubility, an electrolysis precursor compound containing a matrix of low water solubility, and mixtures thereof, for treatment, pretreatment, or post-treatment of tableware in an automatic dishwashing appliance and/or countertop sink reservoir can be used in conjunction with the electrolysis process of the present invention.

The method of use can also incorporate the steps of providing and dispensing a bleach-scavenging agent to deactivate the halogenated mixed oxidants that were generated by the electrolysis process. The chlorine bleach-scavenging agent can be released subsequent to the period of electrolysis, or during one or more of the rinses to deactivate the above-mentioned halogenated mixed oxidants.

Though recirculation of the wash and/or rinse liquor provides for continuous production of newly electrolyzed halogenated mixed oxidants that will be available immediately during specific times of the wash and/or rinse cycles, it can be highly preferred to use the electrolyzed electrolytic solution immediately after the electrolysis, since the beneficial biocidal halogenated mixed oxidants have a short life span. Preferably, the aqueous electrolytic solution, when used for disinfection, sanitization or sterilization, can be used within about 15 minutes, preferably within about 5 minutes, more preferably within about 1 minute, and most preferably almost immediately, after electrolysis.

The device can be preprogrammed to operate according to a specific wash and/or rinse cycle during operation of a specific automatic dishwashing appliance or can be controlled manually to provide a continuous source of electrolyzed water. A timer can be activated to start and stop the electrolysis process. The timer can be mechanical, electrical or electronic. A sensor can also be employed to activate or deactivate the electrolysis process according to a specific time period during the wash and/or rinse cycle of the appliance.

Disposable and/or Replaceable Unattached Electrolytic Device and/or Components

Another embodiment of the present invention relates to an unattached electrolytic device wherein the unattached electrolytic device can be disposable and/or replaceable. Another embodiment of the present invention relates to an unattached electrolytic device wherein any of the device's components, including the electrochemical cell, are disposable and/or replaceable via a refill and/or a replacement cartridge removable from the at least one compartment of the unattached electrolytic device.

An Article of Manufacture

The present invention can also comprise an article of manufacture comprising a refill or replacement of the optional replaceable components of the recirculating device. The replaceable components can be selected from the group consisting of an electrochemical cell refill or replacement cartridge, liquid electrode cleansing composition, at least one product refill or replacement cartridge, filter, elastomeric slit valve, and combinations thereof.

The product refill or replacement cartridge can comprise the following composition, compound, and matrix, including, but not limited to, chloride ions, chlorite ions, water-soluble salts having the formula $(M)_x(XO_2)_y$ and/or $(M)_x(X)_y$ wherein X can be Cl, Br, or I and wherein M can be a metal ion or cationic entity and wherein x and y are chosen such that said salt can be charge balanced, electrolysis precursor compounds, electrolysis precursor salts with low water solubility, electrolysis precursor compounds contained within a medium for controlled release, electrolyzed water, detergent compositions, rinse aid compositions, electrode cleaning agents, bleach-scavenging agents, and metal-protecting agents. The product in the product refill or replacement cartridge can be provided in a dry state as granular, powder, tablet, or pellet forms, or, as a liquid or gel, or in solution, such as an aqueous electrolytic solution, or combinations thereof. The product can be housed in a porous basket for placement in the rack of an automatic dishwashing appliance.

The article of manufacture can also comprise a separate composition in a form such that once placed inside a dishwashing appliance it provides a controlled release of electrolysis precursor salts into the wash and/or rinse liquors during operation of an automatic dishwasher over a period of several weeks or months of regular household and/or commercial use.

What is claimed is:

1. An automatic dishwashing appliance comprising a washing compartment having a washing basin, a tableware rack located within the washing compartment, a first unattached electrolytic device located on the tableware rack and configured to treat tableware, a second, non-buoyant unattached electrolytic device at least partially immersed in a fluid in the washing basin, and injection openings coupled to a rotary nozzle disposed underneath the tableware rack, wherein the first unattached electrolytic device and the second, non-buoyant unattached electrolytic device provide an improvement in cleaning, sanitizing, and/or stain removal, and each comprises:
   (a) a body comprising at least one inlet port for collecting an aqueous electrolytic solution provided by said washing basin;
   (b) an electrochemical cell, located within said body, comprising at least one inlet opening and one outlet opening, and at least one pair of electrodes defining a cell gap comprising a cell passage formed therebetween through which said aqueous electrolytic solution can flow; and
   (c) a source of electrical current supply for providing electrical current between said pair of electrodes;
   wherein the injection openings are configured to deliver said aqueous electrolytic solution to the first unattached electrolytic device on the tableware rack.

2. An automatic dishwashing appliance according to claim 1, wherein said first unattached electrolytic device comprises an electrolytic composition comprising recirculated wash and/or rinse liquor provided by said appliance, and wherein at least some of said recirculated wash and/or rinse liquor is electrolyzed.

3. An automatic dishwashing appliance according to claim 1, wherein said gap between said at least one pair of electrodes has a gap spacing between about 0.1 mm to about 5.0 mm; and wherein the operating voltage is between about 1 and about 12 volts.

4. An automatic dishwashing appliance according to claim 1, wherein said electrochemical cell is non-partitioned.

5. An automatic dishwashing appliance according to claim 1, wherein said unattached electrolytic device is disposable.

6. An automatic dishwashing appliance according to claim 1, wherein said electrochemical cell is replaceable.

7. An automatic dishwashing appliance according to claim 6, wherein said electromechanical cell is rechargeable via a refill and/or a replacement cartridge removable from said at least one compartment of said unattached electrolytic device.

8. An automatic dishwashing appliance according to claim 1, wherein said unattached electrolytic device further comprises a means for activating and/or deactivating said electrochemical cell at specific time intervals throughout the wash and/or rinse cycles of said appliance.

9. An automatic dishwashing appliance according to claim 8, wherein said means of activation and/or deactivation of said electrochemical cell is selected from among the group consisting of timer, sensor, and combinations thereof, and wherein said sensor is optionally capable of analyzing or detecting a composition of a fluid or gaseous environment of said unattached electrolytic device or within said appliance, and signaling said unattached electrolytic device to activate or deactivate said electrochemical cell.

10. An automatic dishwashing appliance according to claim 9, wherein when said fluid or gaseous environment of said unattached electrolytic device or within said appliance comprises a volatile compound or gas selected from the group consisting of perfumes, perfume raw materials, volatile organic compounds, gases comprising oxides of carbon, sulfur, or nitrogen, and mixtures thereof, and when said at least one sensor detects said volatile compound or gas in said unattached electrolytic device or within said appliance, said sensor electrically signals said unattached electrolytic device to activate or deactivate said electrochemical cell.

11. An automatic dishwashing appliance according to claim 1, further comprising a filtering means to minimize fouling of said electrochemical cell from the flow of said recirculated electrolytic solution through said cell passage.

12. An automatic dishwashing appliance according to claim 11, wherein said filtering means comprises a filter removably housed in or attached to said body, wherein said filter is disposable and/or replaceable.

13. An automatic dishwashing appliance according to claim 1, further comprising means for cell regeneration to extend the operating life of said at least one pair of electrodes by descaling or unfouling said at least one pair of electrodes.

14. An automatic dishwashing appliance according to claim 13, wherein said electrochemical cell regeneration means comprises a liquid electrode cleansing composition selected from the group consisting of an anticorrosion agent, descaling agent, and mixtures thereof, wherein said cell passage may further comprise said liquid electrode cleansing composition.

15. An automatic dishwashing appliance according to claim 1, wherein said electrochemical cell comprises a cathode of stainless steel and an anode of titanium, and wherein said anode is coated and/or layered with at least one of the materials selected from the group consisting of platinum, ruthenium, iridium, and oxides, alloys, and mixtures thereof.

16. An automatic dishwashing appliance according to claim 15, wherein said cell passage of said robust cell forms a gap between said at least one pair of electrodes having a gap spacing between about 0.1 mm to about 0.5 mm; and wherein the operating voltage is between about 3 and about 6 volts.

17. An automatic dishwashing appliance according to claim 1, further comprising a cell regeneration means to extend the operating life of said at least one pair of electrodes by descaling or unfouling said at least one pair of electrodes.

18. An automatic dishwashing appliance according to claim 17, wherein said electrochemical cell regeneration means comprises periodic addition of a liquid electrode cleansing composition through said cell passage of said electrochemical cell, wherein said liquid electrode cleansing composition is selected from the group consisting of an anticorrosion agent, descaling agent, and mixtures thereof said unattached electrolytic device.

19. An automatic dishwashing appliance according to claim 18, wherein said liquid electrode cleansing composition is vinegar.

20. An automatic dishwashing appliance according to claim 17, wherein said electrochemical cell regeneration means comprises a means for periodically reversing the polarity of said at least one pair of electrodes.

21. An automatic dishwashing appliance according to claim 1, wherein said source of electrical current supply is achieved by one or more rechargeable electrical batteries.

22. An automatic dishwashing appliance according to claim 21, further comprising at least one sealed or sealable compartment wherein said battery is integrated within said unattached electrolytic device via said at least one sealed or sealable compartment.

23. An automatic dishwashing appliance according to claim 1, wherein said discharge effluent is released outside the device through said outlet port by means of a pump located within said unattached electrolytic device.

24. An automatic dishwashing appliance according to claim 23, further comprising at least one additional and separate, sealed or sealable compartment, wherein said pump is housed in said separate compartment within said unattached electrolytic device.

25. An automatic dishwashing appliance according to claim 1, wherein a discharge effluent is released outside said unattached electrolytic device and into said washing basin of said appliance through said outlet port by gravity flow.

26. An automatic dishwashing appliance according to claim 1, further comprising a storage means for storing at least one product prior to its release.

27. An automatic dishwashing appliance according to claim 26, wherein said storage means comprises at least one sealed or sealable compartment in said unattached electrolytic device for containing said at least one product, such that said at least one product is released in conjunction with at least one predetermined point in time during the wash and/or rinse cycle of said appliance, wherein said at least one sealed or sealable compartment can house at least one product in the form selected from the group consisting of a tablet, free-flowing gel, free-flowing powder, free-flowing liquid, or combinations thereof, and wherein said at least one compartment is recloseable such that the compartments contents are not contaminated by an external medium.

28. An automatic dishwashing appliance according to claim 27, further comprising at least one replaceable component, wherein said at least one product is in the form of a product refill or replacement cartridge.

29. An automatic dishwashing appliance according to claim 27, wherein said means to ensure that the compartment's contents are not contaminated by an external medium is a one-way valve which allows products to flow outside but avoids contamination of the interior of said compartment from an outside medium.

30. An automatic dishwashing appliance according to claim 29, further comprising at least one replaceable component, comprising said one-way valve in the form of a disposable and/or replaceable elastomeric slit valve.

31. An automatic dishwashing appliance according to claim 26, wherein said at least one product comprising said aqueous electrolytic solution selected from the group consisting of chloride ions, chlorite ions, water-soluble salts having the formula $(M)_x(XO_2)_y$ and/or $(M)_x(X)_y$ wherein X is Cl, Br, or I and wherein M is a metal ion or cationic entity and wherein x and y are chosen such that said salt is charge balanced, electrolysis precursor compounds, electrolysis precursor salts with low water solubility, electrolysis precursor compounds contained within a medium or matrix for controlled release, electrolyzed water, detergent compositions, rinse aid compositions, electrode cleaning agents, bleach-scavenging agents, metal-protecting agents, adjunct ingredients, and mixtures thereof.

32. An automatic dishwashing appliance according to claim 31, wherein said bleach-scavenging agent or said metal-protecting agent is selected from the group consisting of perborate, percarbonate, ascorbic acid or derivatives thereof, carbamate, ammonium, sulfite, bisulfite, aluminum tristearate, sodium silicate, benzotriazole, amines, amino acids, and mixtures thereof.

33. An automatic dishwashing appliance according to claim 26 wherein said at least one product is not contained within a resealable compartment but rather is in direct fluid contact with wash and/or rinse liquors for at least some period of time during operation of said appliance.

34. An automatic dishwashing appliance according to claim 1, wherein said unattached electrolytic device further comprises means for communicating to the consumer when it is time to refill or replace said electrochemical cell cartridge.

35. An automatic dishwashing appliance according to claim 34 wherein said communication means comprises an indicator for communicating to the consumer when it is time to refill or replace said electrochemical cell cartridge.

36. An automatic dishwashing appliance according to claim 1, wherein said unattached electrolytic device further comprises a disposable and/or replaceable self-contained source of chloride or chlorite ions.

37. An appliance according to claim 1, wherein said appliance is a commercial dishwasher selected from the group consisting of conveyor-low-temperature type, cabinet-low-temperature type, and combinations thereof.

38. according to claim 37, wherein said source of electrical current supply is the building electrical outlet, wherein said device comprises a power cord and plug for connection to said electrical outlet to allow for higher levels of bleaching species to be generated.

39. according to claim 38, wherein disinfectancy can be achieved in the wash and/or rinse liquor at water temperatures below 48° C.

* * * * *